(12) United States Patent
Siwoff

(10) Patent No.: US 11,642,068 B2
(45) Date of Patent: *May 9, 2023

(54) DEVICE AND METHOD TO DETERMINE OBJECTIVELY VISUAL MEMORY OF IMAGES

(71) Applicant: Ronald Siwoff, Chester, NJ (US)

(72) Inventor: Ronald Siwoff, Chester, NJ (US)

( * ) Notice: Subject to any disclaimer, the term of this patent is extended or adjusted under 35 U.S.C. 154(b) by 377 days.

This patent is subject to a terminal disclaimer.

(21) Appl. No.: 17/109,294

(22) Filed: Dec. 2, 2020

(65) Prior Publication Data

US 2021/0076970 A1 Mar. 18, 2021

Related U.S. Application Data

(62) Division of application No. 15/669,601, filed on Aug. 4, 2017, now Pat. No. 10,888,241.

(Continued)

(51) Int. Cl.
*A61B 5/378* (2021.01)
*A61B 5/00* (2006.01)
(Continued)

(52) U.S. Cl.
CPC .............. *A61B 5/378* (2021.01); *A61B 5/291* (2021.01); *A61B 5/316* (2021.01); *A61B 5/48* (2013.01);
(Continued)

(58) Field of Classification Search
CPC ......... A61B 5/378; A61B 5/291; A61B 5/316; A61B 5/48; A61B 5/7235; A61B 5/7445;
(Continued)

(56) References Cited

U.S. PATENT DOCUMENTS

2014/0228701 A1 8/2014 Chizeck et al.
2015/0133811 A1 5/2015 Suzuki
(Continued)

OTHER PUBLICATIONS

Camisa, John, Leland H. Mylin, and Ivan Bodis-Wollner. "The effect of stimulus orientation on the visual evoked potential in multiple sclerosis." Annals of Neurology: Official Journal of the American Neurological Association and the Child Neurology Society 10.6 (1981): 532-539 (Year: 1981).*

(Continued)

*Primary Examiner* — Andrey Shostak
(74) *Attorney, Agent, or Firm* — Ernest D. Buff & Associates, LLC; Ernest D. Buff

(57) ABSTRACT

Apparatus, system, and computer readable media determine the probability of visual recognition of an image by a subject using electroencephalography (EEG) corresponding to a Visual Evoked Potential (VEP). The apparatus comprises means for presenting a series of visual stimuli corresponding to said image to evoke EEG signals. The visual stimuli of the image are presented in an orientation sequence based on a timing cycle. At least one prism is provided for placement in front of the series of visual stimuli corresponding to said image. The EEG signals evoked in response to said visual stimuli and said prism placed in front of said visual stimuli are recorded and processed by a processor. VEP is generated corresponding to the presence of a shift and thereby provides object statistic reliability of the visual recognition of the image by the subject.

15 Claims, 17 Drawing Sheets

Related U.S. Application Data

(60) Provisional application No. 62/445,632, filed on Jan. 12, 2017.

(51) Int. Cl.
*G02B 5/04* (2006.01)
*A61B 5/291* (2021.01)
*A61B 5/316* (2021.01)
*G02B 7/18* (2021.01)
*G06F 3/147* (2006.01)

(52) U.S. Cl.
CPC .......... *A61B 5/7235* (2013.01); *A61B 5/7445* (2013.01); *G02B 5/04* (2013.01); *G02B 7/1805* (2013.01); *G06F 3/147* (2013.01); *G09G 2380/08* (2013.01)

(58) Field of Classification Search
CPC ......... G02B 5/04; G02B 7/1805; G06F 3/147; G09G 2380/08
See application file for complete search history.

(56) References Cited

U.S. PATENT DOCUMENTS

| | | |
|---|---|---|
| 2016/0116730 A1 | 4/2016 | McCreight, Jr. |
| 2016/0220439 A1* | 8/2016 | Wojciechowski ....... A61B 3/10 |
| 2020/0060573 A1 | 2/2020 | Cohen |

OTHER PUBLICATIONS

Shushtarian, S. M., and Amaneh Norouzi. "Effect of prism induced heterophoria on binocular visual evoked potential." 4th European Conference of the International Federation for Medical and Biological Engineering: ECIFMBE 2008 Nov. 23-27, 2008 Antwerp, Belgium. Springer Berlin Heidelberg, 2009 (Year: 2009).*

ISCEV—J. Vernon Odom—Aug. 2019—ISCEV Standard for Clinical Visual Evoked Potentials (2009 update).

Shushtarian, S. M., and Amaneh Norouzi. "Effect of prism induced heterophoria on binocular visual evoked potential." 4th European Conference of the International Federation for Medical and Biological Engineering. Springer, Berlin, Heidelberg, 2009 (Year: 2009).

* cited by examiner

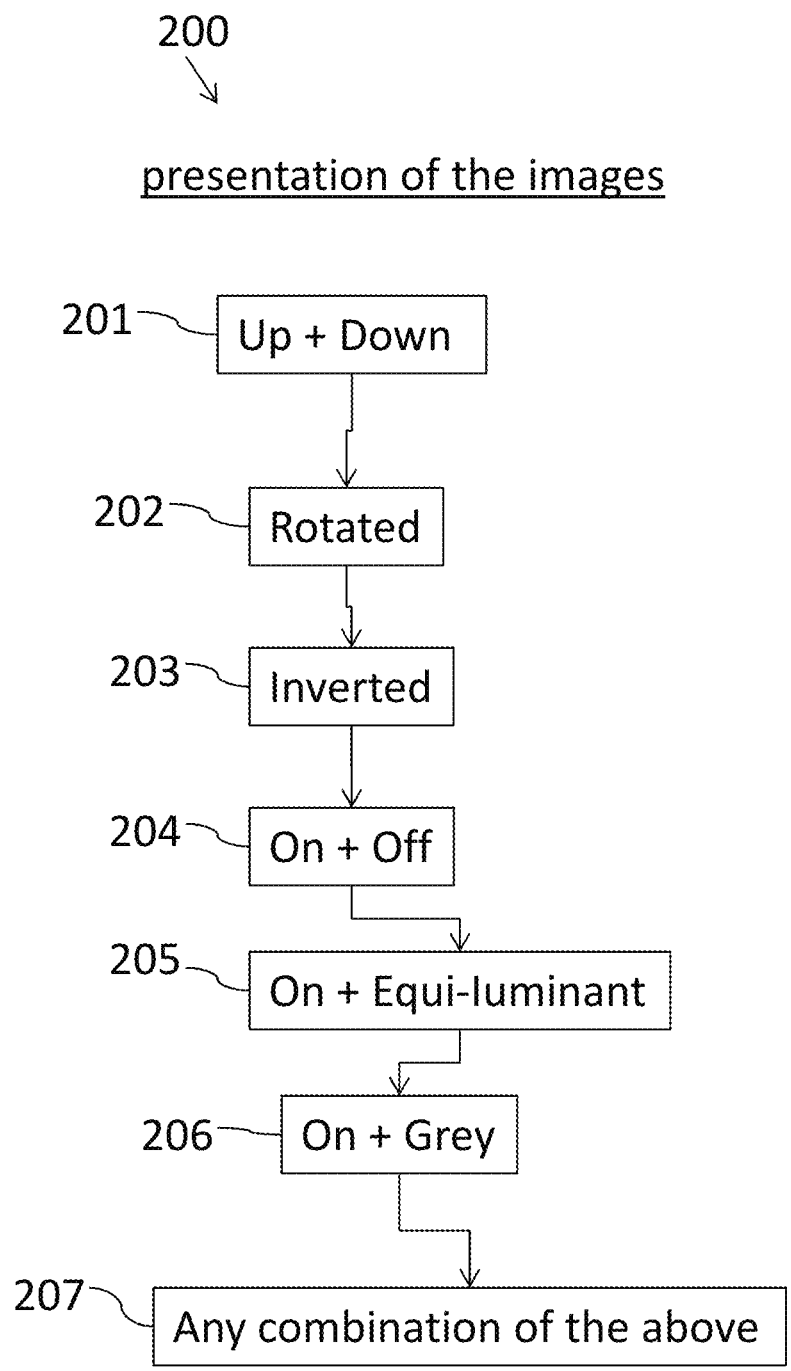

--Prior Art--

--Prior Art--

400

--Prior Art--

425

--Prior Art--

475

--Prior Art--

FIG. 5A

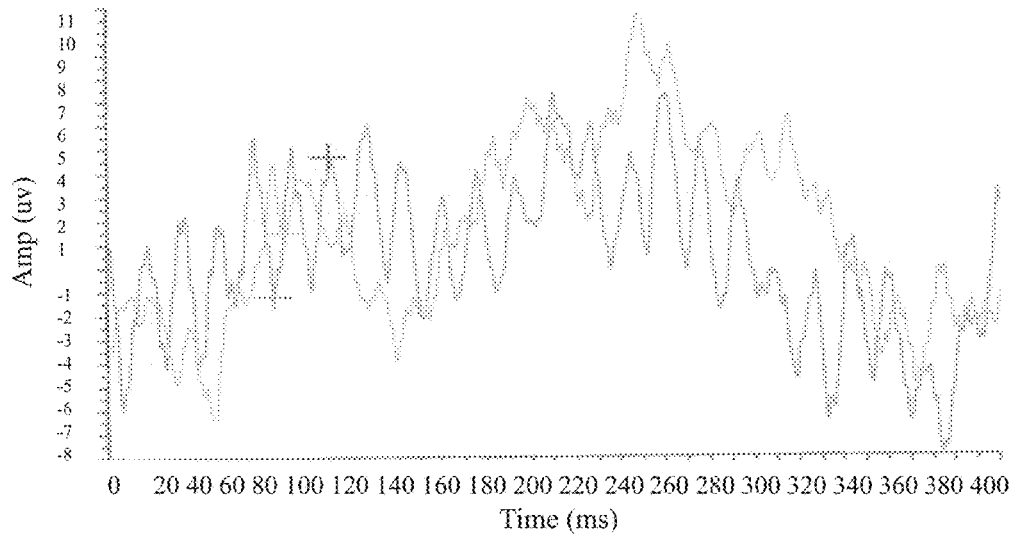

T=15-P=Bill Clinton-OD-85%-F-7/26/2016 3:36:08 PM-NoFilter
T=15-P=Random 2-OD-85%-F-7/26/2016 3:42:35 PM-NoFilter

|  | T=15-P=Bill Clinton-OD-85%-F-7/26/2016 3:36:08 PM-NoFilter | T=15-P=Random 2-OD-85%-F-7/26/2016 3:41:35 PM-NoFilter |
|---|---|---|
| Left Cursor Lat | 74.2 ms | 80.1 ms |
| Amp | -1.24 uV | 1.42 uV |
| Right Cursor Lat | 99.6 ms | 106.4 ms |
| Amp | 4.64 uV | 2.34 uV |
| Delta Lat | 25.4 ms | 26.4 ms |
| Amp | 5.88 uV | 0.92 uV |
| Artifacts | 4 | 1 |
| Eye | OD | OD |
| Test Duration | 15 sec | 15 sec |
| Contrast | 85% | 85% |
| CheckSize |  |  |
| Correction | N | N |
| SWVersion | 2.19.6122 | 2.19.6122 |
| Sensor Value | 141 | 144 |
| Sensor Threshold | 130 | 130 |
| BCVA | 20/20 | 20/20 |
| S/C/Ax/Ad | +2.75/-3.00/10/ | +2.75/-3.00/10/ |

FIG. 5B

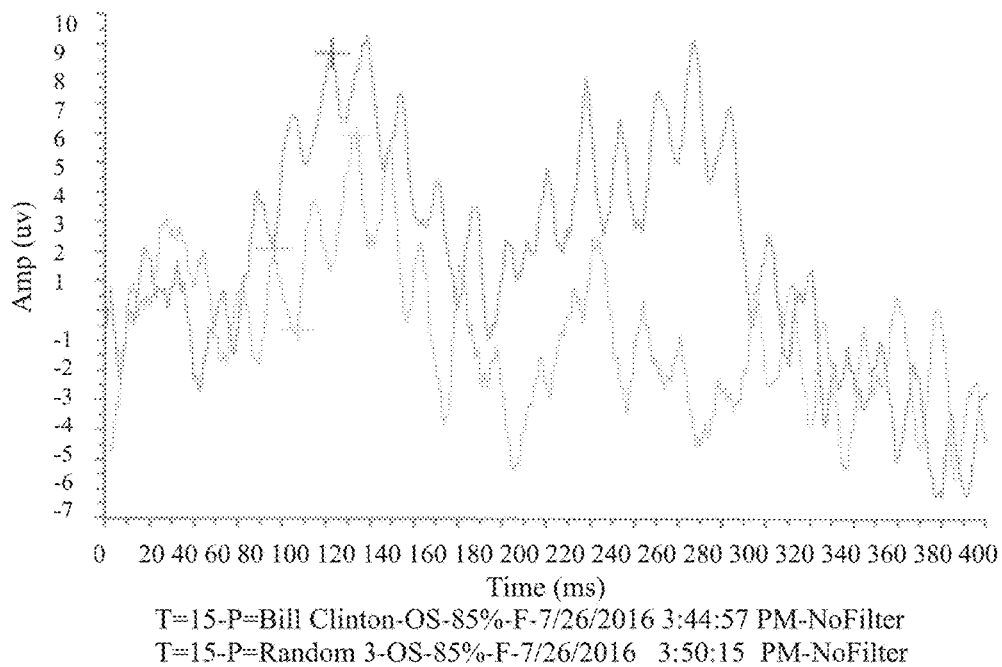

T=15-P=Bill Clinton-OS-85%-F-7/26/2016 3:44:57 PM-NoFilter
T=15-P=Random 3-OS-85%-F-7/26/2016 3:50:15 PM-NoFilter

|  | T=15-P=Bill Clinton-OS-85%-F-7/26/2016 3:44:57 PM-NoFilter | T=15-P=Random 3-OS-85%-F-7/26/2016 3:50:15 PM-NoFilter |
|---|---|---|
| Left Cursor Lat | 76.2 ms | 86.9 ms |
| Amp | 2.05 uV | -0.68 uV |
| Right Cursor Lat | 102.5 ms | 113.3 ms |
| Amp | 8.66 uV | 5.88 uV |
| Delta Lat | 26.4 ms | 26.4 ms |
| Amp | 6.61 uV | 6.56 uV |
| Artifacts | 1 | 0 |
| Eye | OS | OS |
| Test Duration | 15 sec | 15 sec |
| Contrast | 85% | 85% |
| CheckSize |  |  |
| Correction | N | N |
| SWversion | 2.19.6122 | 2.19.6122 |
| Sensor Value | 144 | 134 |
| Sensor Threshold | 130 | 130 |
| BCVA | 20/20 | 20/20 |
| S/C/Ax/Ad | +1.50/-2.25/5/ | +1.50/-2.25/5/ |

FIG. 6A

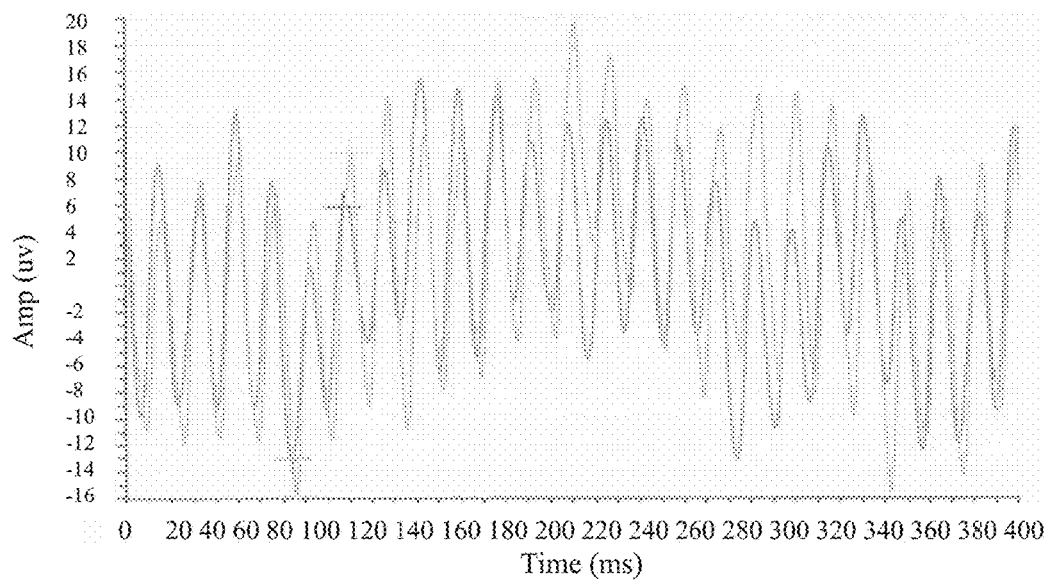

T=15-P=Bill Clinton-OD-85%-F-1/5/2017 11:15:59 AM-NoFilter
T=15-P=Random 2-OD-85%-F-1/5/2017 11:21:17 AM-NoFilter

|  | | T=15-P=Bill Clinton-OD-85%-F-1/5/2017 11:15:59 AM-NoFilter | T=15-P=Random 2-OD-85%-F-1/5/2017 11:21:17 AM-NoFilter |
|---|---|---|---|
| Left Cursor | Lat | 74.2 ms | 76.2 ms |
|  | Amp | -13.10 uV | -15.84 uV |
| Right Cursor | Lat | 97.6 ms | 100.6 ms |
|  | Amp | 5.78 uV | 9.79 uV |
| Delta | Lat | 23.4 ms | 24.4 ms |
|  | Amp | 18.89 uV | 25.64 uV |
| Artifacts | | 0 | 0 |
| Eye | | OD | OD |
| Test Duration | | 15 sec | 15 sec |
| Contrast | | 85% | 85% |
| CheckSize | | | |
| Correction | | N | N |
| SWVersion | | 2.19.6322 | 2.19.6322 |
| Sensor Value | | 184 | 184 |
| Sensor Threshold | | 130 | 130 |
| BCVA | | 20/20 | 20/20 |
| S/C/Ax/Ad | | 0.00/0.00/0/ | 0.00/0.00/0/ |

FIG. 6B

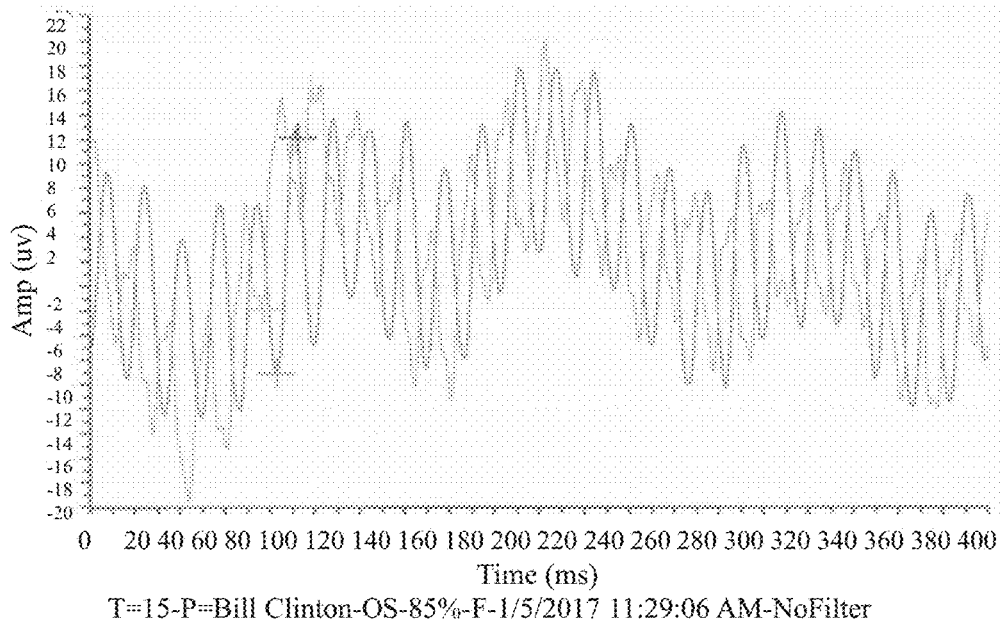

T=15-P=Bill Clinton-OS-85%-F-1/5/2017 11:29:06 AM-NoFilter
T=15-P=Random 1-OS-85%-F-1/5/2017 11:33:58 AM-NoFilter

|  | T=15-P=Bill Clinton-OS-85%-F-1/5/2017 11:29:06 AM-NoFilter | T=15-P=Random 3-OS-85%-F-1/5/2017 11:33:58 AM-NoFilter |
|---|---|---|
| Left Cursor Lat | 83.0 ms | 77.1 ms |
| Amp | -9.17 uV | -3.97 uV |
| Right Cursor Lat | 92.8 ms | 98.6 ms |
| Amp | 10.05 uV | 14.15 uV |
| Delta Lat | 9.8 ms | 21.5 ms |
| Amp | 19.21 uV | 18.12 uV |
| Artifacts | 0 | 0 |
| Eye | OS | OS |
| Test Duration | 15 sec | 15 sec |
| Contrast | 85% | 85% |
| CheckSize |  |  |
| Correction | N | N |
| SwVersion | 2.19.6322 | 2.19.6322 |
| Sensor Value | 181 | 178 |
| Sensor Threshold | 130 | 130 |
| BCVA | 20/20 | 20/20 |
| S/C/Ax/Ad | 0.00/0.00/0/ | 0.00/0.00/0/ |

FIG. 7A

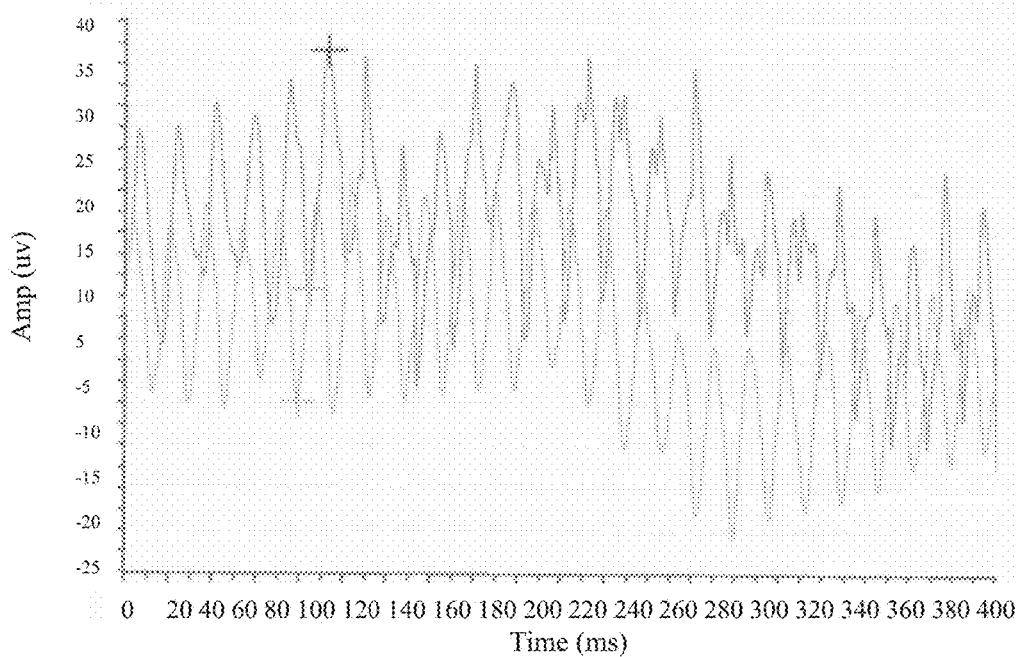

T=15-P=Bill Clinton-OD-85%-F-7/26/2016 2:18:49 PM-NoFilter
T=15-P=Random 1-OD-85%-F-7/26/2016  2:28:08 PM-NoFilter

|  | T=15-P=Bill Clinton-OD-85%-F-7/26/2016 2:18:49 PM-NoFilter | T=15-P=Random 1-OD-85%-F-7/26/2016 2:28:08 PM-NoFilter |
|---|---|---|
| Left Cursor  Lat | 85.0 ms | 79.1 ms |
| Amp | 8.31 uV | -4.93 uV |
| Right Cursor Lat | 92.8 ms | 103.5 ms |
| Amp | 36.61 uV | 21.10 uV |
| Delta  Lat | 7.8 ms | 24.4 ms |
| Amp | 28.31 uV | 26.02 uV |
| Artifacts | 6 | 0 |
| Eye | OD | OD |
| Test Duration | 15 sec | 15 sec |
| Contrast | 85% | 85% |
| CheckSize |  |  |
| Correction | N | N |
| SWVersion | 2.19.6122 | 2.19.6122 |
| Sensor Value | 170 | 123 |
| Sensor Threshold | 130 | 130 |
| BCVA | 20/20 | 20/20 |
| S/C/Ax/Ad | 0.00/0.00/0/0.00 | 0.00/0.00/0/0.00 |

FIG. 7B

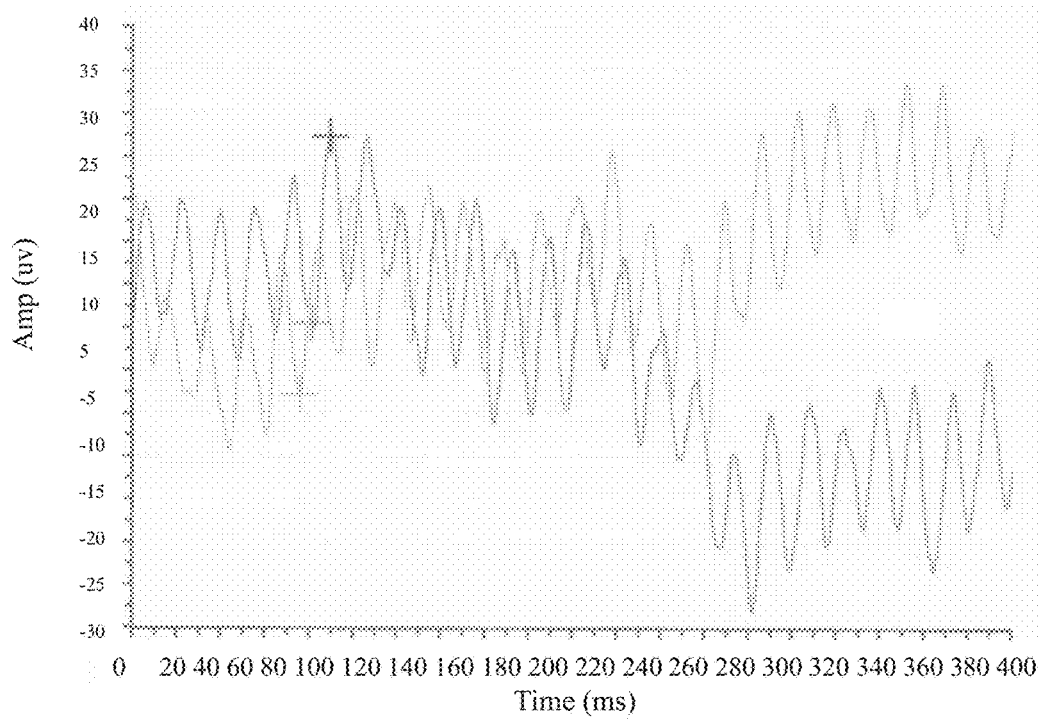

T=15-P=Bill Clinton-OS-85%-F-7/26/2016 2:30:56 PM-NoFilter
T=15-P=Random 3-OS-85%-F-7/26/2016 2:38:18 PM-NoFilter

|  | T=15-P=Bill Clinton-OS-85%-F-7/26/2016 2:30:56 PM-NoFilter | T=15-P=Random 3-OS-85%-F-7/26/2016 2:38:18 PM-NoFilter |
|---|---|---|
| Left Cursor Lat | 81.8 ms | 76.2 ms |
| Amp | 5.38 uV | -2.82 uV |
| Right Cursor Lat | 89.8 ms | 101.6 ms |
| Amp | 27.23 uV | 20.19 uV |
| Delta Lat | 8.8 ms | 25.4 ms |
| Amp | 21.84 uV | 23.81 uV |
| Artifacts | 8 | 7 |
| Eye | OS | OS |
| Test Duration | 15 sec | 15 sec |
| Contrast | 85% | 85% |
| CheckSize |  |  |
| Correction | N | N |
| SWVersion | 2.19.6122 | 2.19.6122 |
| Sensor Value | 127 | 169 |
| Sensor Threshold | 130 | 130 |
| BCVA | 20/20 | 20/20 |
| S/C/Ax/Ad | 0.00/0.00/0/0.00 | 0.00/0.00/0/0.00 |

FIG. 9A

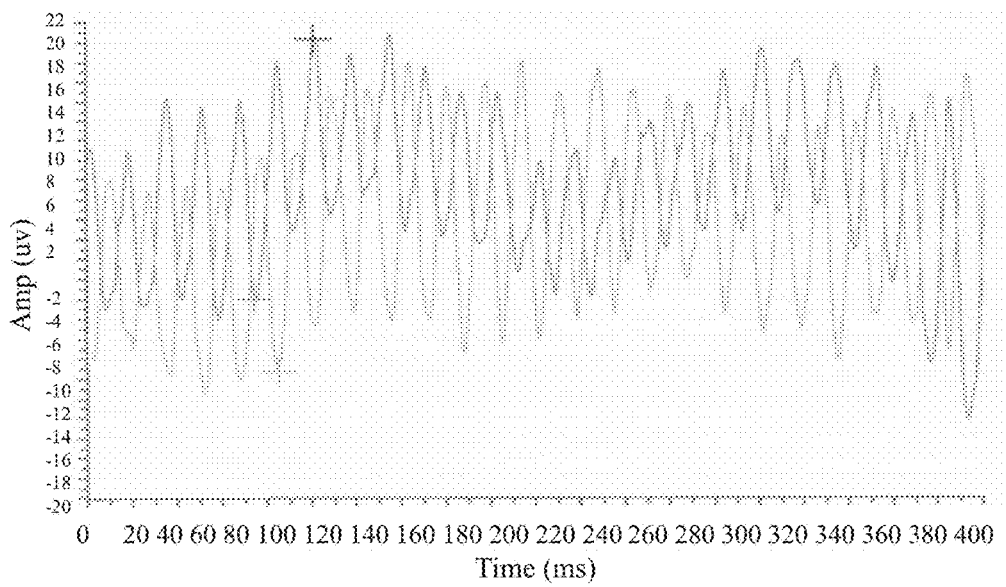

T=10-P=Bill Clinton-OD-85%-F-1/5/2017 10:00:32 AM-NoFilter
T=15-P=Random 1-OD-85%-F-1/5/2017  10:06:37 AM-NoFilter

|  | T=10-P=Bill Clinton-OD-85%-F-1/5/2017 10:00:32 AM-NoFilter | T=15-P=Random 1-OD-85%-F-1/5/2017 10:06:37 AM-NoFilter |
|---|---|---|
| Left Cursor Lat | 74.2 ms | 85.8 ms |
| Amp | -6.07 uV | -13.43 uV |
| Right Cursor Lat | 101.6 ms | 108.4 ms |
| Amp | 20.13 uV | 14.03 uV |
| Delta Lat | 27.3 ms | 23.4 ms |
| Amp | 26.19 uV | 27.45 uV |
| Artifacts | 0 | 0 |
| Eye | OD | OD |
| Test Duration | 10 sec | 15 sec |
| Contrast | 85% | 85% |
| CheckSize |  |  |
| Correction | N | N |
| SWVersion | 2.19.6322 | 2.19.6322 |
| Sensor Value | 193 | 187 |
| Sensor Threshold | 130 | 130 |
| BCVA | 20/50 | 20/50 |
| S/C/Ax/Ad | -1.50/-2.25/180/ | -1.50/-2.25/180/ |

FIG. 9B

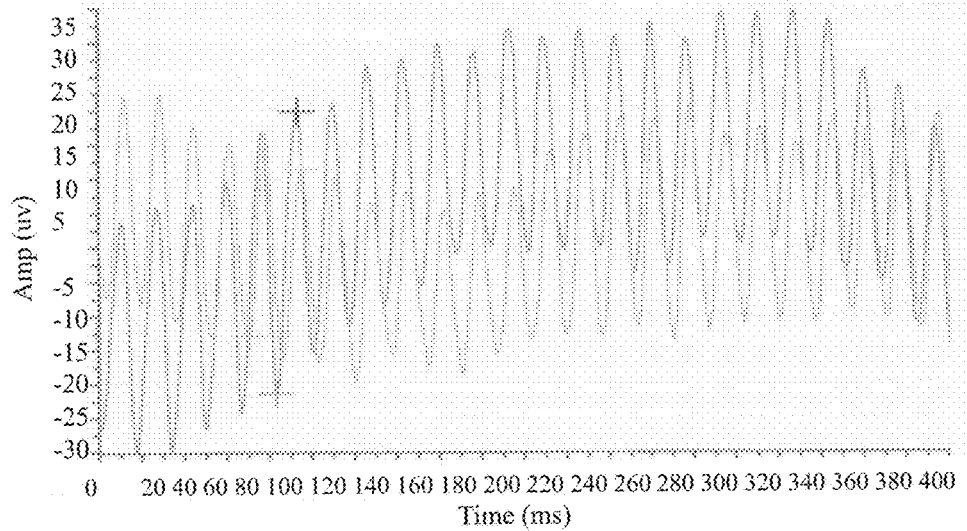

T=15-P=Bill Clinton-OS-85%-F-1/5/2017 10:10:38 AM-NoFilter
T=15-P=Random 2-OS-85%-F-1/5/2017 10:17:31 AM-NoFilter

|  | T=15-P=Bill Clinton-OS-85%-F-1/5/2017 10:10:38 AM-NoFilter | T=15-P=Random 2-OS-85%-F-1/5/2017 10:17:31 AM-NoFilter |
|---|---|---|
| Left Cursor Lat | 83.0 ms | 71.3 ms |
| Amp | -21.45 uV | -12.99 uV |
| Right Cursor Lat | 93.7 ms | 95.7 ms |
| Amp | 19.86 uV | 11.35 uV |
| Delta Lat | 10.7 ms | 24.4 ms |
| Amp | 41.32 uV | 24.35 uV |
| Artifacts | 1 | 0 |
| Eye | OS | OS |
| Test Duration | 15 sec | 15 sec |
| Contrast | 85% | 85% |
| CheckSize |  |  |
| Correction | N | N |
| SwVersion | 2.19.6322 | 2.19.6322 |
| Sensor Value | 190 | 189 |
| Sensor Threshold | 130 | 130 |
| BCVA | 20/20 | 20/20 |
| S/C/Ax/Ad | -2.25/-0.75/150/ | -2.25/-0.75/150/ |

DEVICE AND METHOD TO DETERMINE OBJECTIVELY VISUAL MEMORY OF IMAGES

CROSS-REFERENCE TO RELATED APPLICATIONS

This application is a divisional of applicants' co-pending U.S. patent application Ser. No. 15/669,601 filed Aug. 4, 2017 entitled "DEVICE AND METHOD TO DETERMINE OBJECTIVELY VISUAL MEMORY OF IMAGES", which claims the benefit of Provisional Application No. 62/445,632, filed Jan. 12, 2017, the disclosures of which are hereby incorporated in their entirety by reference thereto.

FIELD OF THE INVENTION

The present invention relates to image recognition and visual evoked potential technology useful in the security, law enforcement and or medical fields; and, more particularly, to a system, apparatus, method and a computer-readable medium that extracts information from a visual evoked potential (VEP), indicating the likelihood that the subject recognizes or has a previous knowledge of an image presented.

BACKGROUND

There is a need in many fields to objectively or quantitatively determine whether a subject recognizes a visual image, including in, for non-exhaustive example, medical, law enforcement and security fields.

Quantification of a person's recognition of a visual image has particular applications in the medical field in treating multiple sclerosis, certain cognitive disorders, such as prosopagnosia, macular degeneration, and vision loss. Prosopagnosia, also called face blindness, is a disorder of face perception where the ability to recognize familiar faces, including one's own face, is impaired, while other aspects of visual processing (e.g., object discrimination) and intellectual functioning remain. Problems such as these are often too subtle or not easily detected during clinical examination.

Objective or qualitative determination s to a subject's recognition of a visual image also has important applications in law enforcement and security. Concerns over terrorism are a global issue. Terrorists and criminals can form networks aiding and abetting one another to facilitate criminal activities. Others who are not themselves part of the terror network are affiliated by way of association or through family connections. As concerns over touristic threats persist, further security technology is continuously sought. Security measures implemented include biometric data technologies that involve using metrics related to human characteristics,5 physiological and/or behavioral, including fingerprint, palm veins, face recognition. DNA, palm print, hand geometry, iris recognition, retina, odor/scent, gait, voice and typing rhythm. Biometric data technologies are currently provided for use in collecting biometric data of an individual for identifying the individual and/or verifying identity in security, consumer and electronic fields.

A variety of approaches have been used in the past to ascertain whether a subject has knowledge of or recognizes a subject or image. Examples include, polygraphs, observation of a. subject's facial expression/body language, change in voice, galvanic skin response, electroencephalography (EEG) which looks at brain activity (alpha, beta, and theta waves), eye tracking, and voice analysis. However, these methods have not proven to be reliable in determining whether a subject recognizes a visual image. Problems with several of these approaches result because they are subjective assessments and assumptions on behavior or control over body parameters can drive test results, rendering them unreliable. Current techniques' reliabilities are also vulnerable to false results as they can be tricked or behaviors masked by the subject. It would be desirable to provide a device and method that can be used to objectively determine whether a subject recognizes an image through qualitative analysis of measured data that is beyond subjective juncture and the control of typical subjects.

Electroencephalography (EEG) measures signals produced by the brain. Electrodes are placed on the scalp, amplified, and recorded. The EEG shows brain activity, it does not indicate whether a subject has any previous knowledge of an image.

A Visual evoked potential (VEP) is derived from processed EEG data. VEPs are produced by presenting a visual stimulus to a subject at the same time EEG data is recorded.

This process is repeated several times and the data is averaged. The result is a VEP. The International Society for Clinical Electrophysiology of Vision (ISCEV) provides guidance regarding the measurement and definition of obtaining VEP's, See, for example, Society for Clinical Electrophysiology of Vision (ISCEV) Guidelines for clinical visually evoked potentials—20176 update, found at VEPO Standard 2016 draft 2016, Feb. 24 jv012.docx02-24. Skilled practitioners can assess the data to help determine impairment in brain function, for example, impairment that could be caused by multiple sclerosis, brain tumors, stroke or other impairment or disease. VEP is also frequently utilized in determining changes in vision, such as macular degeneration or problems along the pathways of certain nerves, it is not currently utilized to assess a subject's prior knowledge of an image. While this data aids in determining impairment, it does not indicate whether a subject recognizes a visual image.

Facial recognition technologies utilize an individual's face compared to a data-base of faces or a previously uploaded image of the individual's face, to identify a match and, by so doing, identify the individual. These systems and methods provide sample digital data to compare an image of a face to a data base of images in a computer. However, such facial recognition technology does not currently provide the ability to determine if an individual associates with, or has memory or knowledge of, other individuals.

There exists a need in the art for a device and method that indicate the likelihood that the subject has a previous knowledge of an image through measurement of involuntary responses of the subject.

SUMMARY OF THE INVENTION

The present invention provides methods, systems, and computer readable medium operable to measure the effects of cortical modification from the brain to the eye to determine whether a subject has a previous memory or knowledge of an image, a person, place, or thing. Advantageously, the present invention provides an objective method, system, and computer readable media operable to extract information from visual evoked potential (VEP) of an individual/subject to determine the likelihood that the subject has memory of/previous knowledge of or recognition of a face and/or an object or place. Uniquely, the present invention probes the effects of memory on facial and/or object recognition by a human and has particular applications in the security and law enforcement field.

In accordance with the invention, an apparatus is provided for determining visual recognition of an image by a subject using electroencephalography (EEG) corresponding to a Visual Evoked Potential (VEP). The apparatus comprises means for presenting a series of visual stimuli corresponding to the image to evoke EEG signals. The visual stimuli of the image are presented in an orientation sequence based on a timing cycle. At least one prism is provided for placement in front of the series of visual stimuli corresponding to the image. The EEG signals that are produced in response to the visual stimuli and the prism placed in front of the visual stimuli are signal averaged and recorded and may be outputted. This is the sensory evoked potential, or in the case of visual stimuli, the Visual Evoked Potential (VEP). The general process and equipment for generating VEP from EEG signals are well known and readily available in the art.

This invention provides an apparatus useful for determining visual recognition of an image by a subject using electroencephalography (EEG) corresponding to a Visual Evoked Potential (VEP), comprising:
  a. means for presenting to a subject to be tested a series of visual stimuli corresponding to said image to evoke EEG signals, said visual stimuli of said image being presented in an orientation sequence based on a timing cycle;
  b. at least one prism adapted to be placed in front of a series of visual stimuli presented to the subject corresponding to said image; wherein EEG signals are evoked in response to said visual stimuli with said prism placed in front of said visual stimuli;
  c. a processor for: (i) converting the EEG signals evoked from the visual stimuli to a VEP; (ii) identifying one or more neurotransmission latency times from said VEP; and i) recording or displaying said neurotransmission latency time from each of two or more images.

The invention also provides a method for determining visual recognition of an image by a subject using electroencephalography(EEG) corresponding to a Visual Evoked Potential (VEP). The method comprises the steps of (1) presenting a series of visual stimuli corresponding to the image to evoke EEG signals, the visual stimuli of the image being presented in an orientation sequence based on a timing e; and (2) presenting at least one prism placed in front of the series of visual stimuli corresponding to the image. The EEG signals evoked in response to the visual stimuli and the prism placed in front of the visual stimuli are recorded and processed by a processor. The VEP is generated corresponding to presence of a shift.

The method for determining latency shift in Visual Evoked Potential between at least two or more images including a target image that is useful for determining visual recognition of the target image, can comprise the steps of (in non-limiting order):
  a. presenting a series of visual stimuli corresponding to said target image to a subject to evoke a first VEP wherein a prism is provided between said target image and said subject, said visual stimuli of said target image being presented in an orientation sequence based on a timing cycle, said target image comprising a person, a place, or an object;
  b. presenting a second series of visual stimuli corresponding to a second image to said subject to evoke a second VEP wherein a prism is provided between said second image and said subject, said second visual stimuli of said second image being presented in an orientation sequence based on a timing cycle, said second image comprising a person, a place, or an object;
  c. recording the first VEP and the second VEP and determining ether there exists a latency shift between the first VEP and the second VEP.

Also provided is a non-transitory computer storage readable medium for determining latency shift in Visual Evoked. Potential (VEP) between two or more images, comprising computer-useable instructions that, when used by one or more computing devices, cause the one or more computing devices to: receive information from electrodes on a subject's scalp generating and recording EEG signals corresponding to synaptic transmission/neurotransmission speed when a subject is presented with a series of visual stimuli corresponding to said image presented in an orientation sequence based on a timing cycle; receive information from electrodes on a subject's scalp generating and recording EEG signals corresponding to synaptic transmission/neurotransmission speed when a subject is presented with at least one prism placed in front of said series of visual stimuli corresponding to said image; wherein EEG signals evoked in response to said visual stimuli and said prism placed in front of said visual stimuli are recorded and processed by a processor to provide a the VEP, and wherein said medium further includes instructions for determining VEP for two or more Images and for determining the presence of a latency shift between said two or more images.

BRIEF DESCRIPTION OF THE DRAWINGS

The invention will be more fully understood and further advantages will become apparent when reference is had to the following detailed description of the preferred embodiments of the invention and the accompanying drawing, in which:

FIG. 2 is a flow diagram showing the presentation of the image presentation and prism directions.

with reference to FIGS. 3A and 3B, the location of active and reference Electrodes for Standard Responses is shown.

FIG. 5A shows the latency for a known image is less than an unknown image. The evoked potential for the right eye for subject P1 is presented. The left eye is patched and a prism is placed in front of the right eye. The prism is the same amount and direction for the known image (Bill Clinton) and the unknown image (Random). The Right Cursor Lat findings show that the latency for the known image is less than that for the unknown image.

FIG. 5B shows the latency for a known image is :less than an unknown image. The evoked potential for the left eye for subject P1 is presented. The right eye is patched and a prism is placed in front of the left eye. The prism is the same amount and direction for the known image (Bill Clinton) and the unknown image (Random). The Right Cursor Lat findings show that the latency for the known image is less than that for the unknown image.

FIG. 6A shows the latency for a known image is less than an unknown image. The evoked potential for the right eye for subject P2 is presented. The left eye is patched and a prism is placed in front of the right eye. The prism is the same amount and direction for the known image (Bill Clinton) and the unknown image (Random). The Right Cursor Lat findings show that the latency for the known image is less than that for the unknown image.

FIG. 6B shows the latency for a known image is less than an unknown image. The evoked potential for the left eye for subject P2 is presented. The right eye is patched and a prism is placed in front of the left eye. The prism is the same amount and direction for the known image (Bill Clinton) and the unknown image (Random). The Right Cursor Lat findings show that the latency for the known is less than that, for the unknown image.

FIG. 7A shows the latency for a known image is less than unknown image. The evoked potential for the right eye for subject P3 is presented. The left eye is patched and a prism is placed in front of the right eye. The prism is the same amount and direction for the known image (Bill Clinton) and the unknown image (Random). The Right Cursor bit findings show that the latency for the known image is less than that for the unknown image.

FIG. 7B shows the latency for a known image is less than an unknown image. The evoked potential for the left eye for subject P3 is presented. The right eye is patched and a prism is placed in front of the left eye. The prism is the same amount and direction for the known image (Bill Clinton) and the unknown image (Random). The Right Cursor Lat findings show that the latency for the known image is less than that for the unknown image.

FIG. 9A shows the latency for a known image is less than an unknown image. The evoked potential for the right eye for subject P5 is presented. The left eye is patched and a prism is placed in front of the right eye. The prism is the same amount and direction for the known image (Bill Clinton) and the unknown image (Random). The Right Cursor Lat findings show that the latency for the known image is less than that for the unknown image.

FIG. 9B shows the latency for a known image is less than an unknown image. The evoked potential for the left eye for subject P5 is presented. The right eye is patched and a prism is placed in front of the left eye. The prism is the same amount and direction for the known image (Bill Clinton) and the unknown image (Random). The Right Cursor Lat findings show that the latency for the known image is less than that for the unknown image.

DETAILED DESCRIPTION THE INVENTION

Figure 1A:
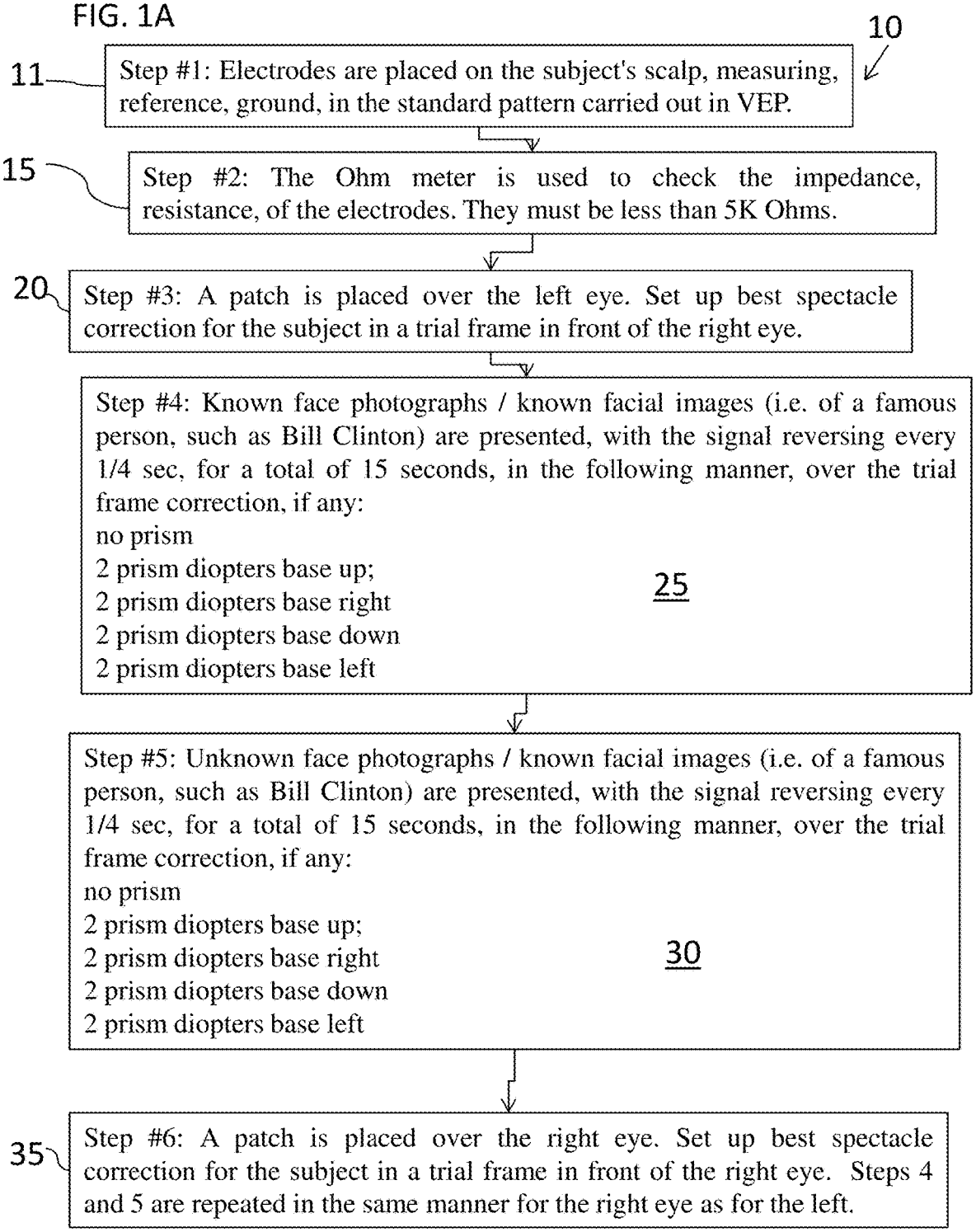
FIG. 1A is a flow diagram showing steps of an embodiment of the method for determining differences in latencies that occur between one particular face and several reference images to establish statistical reliability that the subject has previous knowledge of one or more particular faces.

Apparatus, system, and computer readable media are described herein for determining the probability of visual recognition of an image by a subject using electroencephalography (EEG) corresponding to a Visual Evoked Potential (VEP). In a broad aspect of the invention, there are provided means for presenting a series of visual stimuli corresponding to the image to evoke EEG signals. The visual stimuli of the image are presented in an orientation sequence based on a timing cycle. At least one prism is provided for placement in front of the series of visual stimuli corresponding to the image. The EEG signals evoked in response to the visual stimuli and the prism placed in front of the visual stimuli are recorded and processed by a processor. VEP is generated corresponding to presence of a shift and thereby provide object statistic reliability of visual recognition of the image by the subject.

Images may be faces, images of people, places, animals, and/or objects or things. In general, the image should be of something with which an individual can associate/have a personal relationship. The images are presented to a subject in a visual orientation sequence such that the image presented to the subject person being tested is an orientation sequence shown for a short period of time ('ON' period) and then switched off or altered for a short period of time (both referred to as the 'OFF' period), with this timing and cycle being repeated to create the orientation sequence. The individual visual ON and ALTERED orientations are shown one at a time, but for short periods of time, corresponding to individual ON phase and ALTERED phases during the orientation timing sequence. The reference visual image that is being tested can be used as the ON image, also referred to as the reference orientation. The ALTERED image can be, for example, a visual alteration of the reference orientation or a non-specific image such as a blank screen, a solid colored (e.g., gray, white, black, or other color) screen. If two visual orientations are used, the images are flashed back and forth between a reference image being evaluated (ON image) and an ALTERED image. If desired, two or more different ALTERED images can be used in the ALTERED phase of the orientation sequence, In this case one ALTERED image is shown at a time before returning to the reference or ON image. The ALTERED image or phase of the visual orientation sequences can include can (but are not limited to), upside-down, inside-out, inverted (upside-down and inside-out), rotated (e.g., 45, 90, or other number of degrees), solid or blank images (including but not limited to white, gray, black, or any other color), patterned, abstract, and combinations thereof.

Current International Society for Clinical Electrophysiology of Vision (ISCEV) Guidelines provides guidance regarding the measurement and definition of stimulus parameters for VEP's. See Society for Clinical Electrophysiology of Vision (ISCEV) Guidelines for clinical visually evoked potentials—20176 update, found at VEPO Standard 2016 draft 2016, Feb. 24 jv012.docx02-24.

The stimuli may be generated on a screen with the viewing distance, typically between 50 cm and 150 cm, adjusted to a suitable field size for any physical size of display screen. Mean photopic luminance of 50 cd/m$^2$ (with an acceptable obtained using a reversal rate of 2.0±0.2 reversals per second (rps). [This corresponds to 1.0±0.1 Hz, as a full cycle, includes two reversals].

The ON and ALTERED visual images in the orientation sequence are preferably substantially equi-luminant, or of equal brightness or equally luminant, allowing for minor changes in mean luminance during transition between images or image orientations in order to minimize or avoid any impact on VEP data. By substantially equi-luminant, it is meant that any difference in the luminance of the ON and ALTERED images presented should be 10% or less, preferably 5% or less, preferably 2% or less.

The phototropic luminance used in this invention can vary widely, although it is preferably maintained consistent for a particular evaluation, as described above. A mean photopic luminance of 50 cd/m$^2$ (with an acceptably low variation) can be used, although both higher and lower luminance values can be used. Luminance values useful for measuring VEP are also reported by Society for Clinical Electrophysiology of Vision (ISCEV) Guidelines for clinical visually evoked potentials—20176 update, found at VEPO Standard 2016 draft 2016, Feb. 24 jv012.docx02-24.

Data is collected only when the image is presented to a subject. The data is collected many times and averaged. The resulting VEP is produced by the image presented to the subject. The processor automates the analysis of the VEP (Visual Evoked Potential). None of the functions of "the processor" are standard for a conventional VEP. The invention is comparing images of persons, places, or things, and therefore the result is not a conventional VEP output. The VEPs generated for the image with and without the prism are compared. It has been found that the VEP latency for an unknown image, when seen through a prism, is slower than the VEP of a known image, seen through the same prism. If latencies are the same, then it is likely the subject has previous knowledge of the image. Conventional VEPs use checkerboard patterns, flashing lights, sine wave gratings, and square wave gratings varying in spatial frequencies. The use of images is novel to this invention. The introduction of a prism in front of the eye has been found to change neurotransmission speeds. This is also novel to this invention. This change is reduced or canceled out if a subject has a previous knowledge of the image. The VEP produced by an image is compared to the VEP of the same image seen through the prism.

During VEP measurement, data is collected for the test subject's response to visually observing the reference or ON image. The VEP is measured in order to identify the P-100 Latency data point generated as a result of the test subject visually processing the reference or ON image. In order to ensure that the P-100 Latency is observed, the ON phase should last long enough to record the corresponding data. As will be well understood by those skilled in the art, the P-100 Latency refers to the peak in the VEP data that typically occurs at about 100 milli-seconds after exposure to a visual stimulus. For any individual oar exposure to a visual stimulus, the actual peak reflected in the data can vary above or below 100-milli-seconds, depending on the physiology of the subject, the image that is shown, and the image presentation variables including those discussed herein. Data is recorded for each ON phase in the orientation timing sequence and used in the calculation of the VER Since P-100 Latency can vary by individual and by image, in general it is preferred for the duration of the ON phase to be at least 100 ms, or at least 110 ms, or at least 150 ms, or at least 200 ms. The image duration can be up to 300 ms or less, or 250 ins or less, or 200 ms or less. The ON phase can be in the range of 100 ms to 250 ms. Thus, the duration of time for the ON phase can be from 100-300 ms, 110-250 ms, or 150-250 ms, or 200-250 ms. Longer phases are possible but require additional time while not providing additional data relevant the P-100 Latency. The duration of the ALTERED phase can be within the same minimums maximums, d ranges as the ON phase. It is not necessary for the ON duration to be the same as the ALTERED duration, however the ON and ALTERED durations can be the same. Data can be collected for a portion of the ON phase, or for the entire ON phase, however data collection should be long enough o ensure that the P-100 Latency data is recorded so it is preferred to record for at least 100 ms, or 110 ms, or 150 ms, or 200 ms. Thus, for example, image duration can be 250 ms ON separated by 250 ms ALTERED, and data recorded for the first 240 ms of the ON phase.

The stimulus rate, which is the rate of alternating the images between the selected visual orientations, can also vary corresponding to the image ON and ALTERED phase durations, but can generally be 2.0+/−0.2 changes (or reversals per second; or per 1000 ms) This corresponds to 1.0±0.1 Hz, as a full cycle includes two reversals [For non-limiting representative example: Full cycle of two reversals @ 1 Hz=1000 ms: reversal #1 →ON for 250 ms , ALTERED for 250 ms; reversal #2→ON for 250 ms ALTERED for 250 ms=1000 ms or 1 Hz cycle for full cycle of two reversals]. This is the same rate recommended according to the Society for Clinical Electrophysiology of Vision (ISCEV) Guidelines for clinical visually evoked potentials—20176 update, found at VEPO Standard 2016 draft 2016, Feb. 24 jv012.docx02-24.

The present invention probes the effects of memory on images recognition by a human. An apparatus or system can comprise electrodes, a signal amplifier, an analog to digital converter, a computer processor, software or programming to convert EEG signal data to a VEP and software or programming to analyze the processed data (VEP). The apparatus or system further can comprise means for providing images for presentation to a subject who is to be tested and a means for presenting the images to the subject. Means for presenting includes a display screen, displaying images electronically generated and/or transmitted or projected thereon. Virtual reality type devices, including wearable devices, are also contemplated. A personal computer, including a laptop computer, or other processing device can be used for providing the images, including storing images or obtaining or receiving images from other data sources including but of limited to other databases, internet sources including but not limited to social media and physical photographs, drawings, or other images. The invention can also include a projector for presenting the images to the subject to be tested. The projector can be, for non-limiting example, the screen from a computer, which optionally may be the same computer that is used to provide and/or process the it ages and data, or a separate projector including without limitation a separate screen or a projector integrated into or attached to glasses that could be worn by the subject to be tested, Signal averaging is carried out after the data is converted to a digital format. A signal averaging processor extracts the data that is a time-locked response to the image from the raw signal in order to remove the signals that are not responses to the image presented. The processor then averages the extracted data produced by the visual cortex to produce a visual evoked potential (VEP). Prisms are placed in front of the subject's eye, in order to change the time it takes for signals to arrive at the occipital cortex, the primary visual cortex in the brain. Signal averaging may be carried out for a single prism direction where the signals resulting from the image sequence are averaged together, and then a standard deviation is calculated.

This is done for a known image, or a reference image (such as a known person or known place or thing).

The reference image can be selected to be an image that the person administering the evaluation knows or has reason to believe that the test subject has a high degree of familiarity. For instance, the reference image could be a photo of the test subject him- or her-self, or a family member. Such reference images can be obtained from a variety of sources including but not limited to the test subject him- or her-self, or social media associated with the test subject. Then, the same thing is done for a second image (which may be a target image or an image that is being sought to determine if the subject has recognition thereof). If the standard deviations are close, it is determined that the subject knows or recognizes the second image. If they are not close, then it is likely the subject does not know or recognize the second image.

Latency of neurotransmission of the image may be different for the same image and image orientation using different prism directions. Different prism directions can be achieved in a number of ways. In one contemplated manner, the prism itself is fixed, but the angle of light entering the prism is adjusted. In a more preferred arrangement, adjustable optical mounts are used to mount or position prisms so that the prisms can be rotated and/or moved. A number of securing methods are contemplated, such as bar, ring, kinematic, or gimbal to safely hold optical components, including one or more prisms, without risk of damage or unwanted movement. Preferably, one or more prisms are mounted in a manner providing height, left, right, up, down adjustment, and/or rotation on the prism axis by 180°. Non-limiting examples of devices for mounting and adjusting prisms can be found, for representative example in U.S. Pat. No. 5,267,089 to Yamamoto et al. and U.S. Pat. No. 4,088,396 to Edelstein.

A larger difference between neurotransmission latency between a reference image and an image that the subject does not recognize is preferred over prism directions that have less difference in latency. When this is identified, the it is preferred to use the prism direction with the greater latency for future testing (e.g., with additional images) of the same subject.

Output data are numbers that are then used to assess recognition. Finally, the data of known and unknown faces or objects are used to determine the statistical probability that a face is known to a subject. The signals derived from the eye to the brain are referred to as synaptic transmission. Previous memory of a face presented sends signals to the sensory organs that modify the sensory data, resulting in a change in neurotransmission speed, which offsets the expected changes produced by prisms. In the case of previous memory, the brain responds with a faster response than expected from exposure to random unknown faces. This effect is referred to as ephaptic transmission.

Without being bound by theory, it is believed that flashing images with the stimuli are modified by rotating, etc because EEG signal shift that represents a latency shift indicates recognition of the image. Multiple prism directions are used (at least 1 or at least 2, but oftentimes more are used). Prisms bend light toward the base of the prism. The prism is moved in the direction of the apex of the prism. Various orientations of the prism can be used to minimize the effect of retinal disease or neurological disease on the evoked signals. Retinal disease tends to align itself along the horizontal axis. Neurological disease tends to align itself along the vertical axis. Using multiple prism directions cancels out the effects produced by retinal and neurological diseases on interpolation of the signals.

Protocols of standard VEP have applications in assessments of function of the eye and/or optic nerves anterior to the lateral geniculate body (i.e. prechiasmal function) as well as post-chiasmal pathways to the occipital visual cortex. VEP measures the amount of time that results for a visual stimulus to travel from the ere occipital cortex in order to determine whether there are abnormalities in the nerve pathway. Light-evoked signals, small in amplitude and hidden within the normal electroencephalographic (EEG) signal, are amplified by repetitive stimulation and time-locked, signal-averaging techniques, separating it from the background EEG readings.

Image recognition is utilized in the subject method in order to determine cortical information processing in the brain. Because it has been found that the prism produced a change in neurotransmission speed of an image most effectively if the image is unknown to the individual or subject being tested. If the image is known to the individual there is no significant shift or slowing in neurotransmission speed compared to the VEP data produced with no prism. This is an example of "ephaptic" transmission. Ephaptic transmission is the modification of neurotransmission signals by the cortex of the brain. The familiarity of an image is believed to play a role in the perception of images and therefore cognitive and visual function. Recorded event-related potentials in the brain have been found to determine cognitive timing of recognition of images. The use of a prism is critical to produce a second set of data compared to the recording of original of the same image data without the prism. The shift in latency produced by prisms occurs with conventional VEP testing as well as Image Evoked Potentials. What s unique to the invention is that memory of the image can cancel or diminish this latency shift.

The electrodes can be placed on the subject's scalp, recording signals that are amplified, digitized, signal-averaged, analyzed for reliability, and then filtered to remove extraneous 60 Hz noise, alpha waves, and unreliable data, finally displaying the visual evoked potential. A latency shift is produced by inserting a prism in a trial frame in front of the subject's eye. The prism is positioned in front of the subject's eye and between the subject, and the image, such that the subject still sees the image. As previously discussed the prism bends light, thereby affecting the VEP data compared to the data where no prism is used for images that are not the subject. At least one prism orientation or direction is used in the invention. The use of multiple prism orientations or directions may also be used. The use of multiple prism directions is useful to reduce the possibility of false positives or false negatives that could otherwise occur due to retinal or neurological disease or condition impacting certain regions of an eye. By using multiple prism directions, the VEP data may indicate recognition for only one or certain of the prism orientations, while not indicating recognition for other orientations. When the latency shift is due to retinal or neurological disease or condition, alternate orientation of the prism may be achieved by turning it in different directions. Light and images are bent in the direction of the base of the prism. If the image falls on a retinal scar or a scotoma produced by neurological disease, the analysis of the data could be difficult. The use of multiple prism direction is an attempt to minimize the effects of possible retinal or neurological disease that produces blind spots, (scotomas). Each prism direction or orientation, bending the light up, down, left, right of the center of the retina) results in an evoked potential reading. Additional prism orientations may also be tested by adjusting the angle of the light entering the eye. When combined, they produce a range of latencies. The prism direction that results in the shortest latency for a known image is used for an unknown image. It has been found that the latencies significantly decrease when the subject has a previous memory of the image, regardless of the intervention of prism. The differences in latencies that occur between one particular image and several reference images establishes statistical reliability that the subject has previous knowledge of one or more particular faces.

Skin electrodes such as sintered silver-silver chloride, standard silver-silver chloride, or gold cup electrodes are recommended for recording VEPs. The skin should be prepared by cleaning and a suitable paste or gel used to ensure good, stable electrical connection. The electrode-skin contact impedances should be below 5 K Ohm as measured between 20 and 40 Hz. To reduce electrical interference, electrode-skin contact impedances should differ by no more than 1 K Ohm between electrodes. Typically, electrodes are placed on the scalp relative to bony landmarks, in proportion to the size of the head. The anterior/posterior midline measurements are based on the distance between the nasion and the inion over the vertex. The active electrode is placed on the occipital scalp over the visual cortex at Oz with the reference electrode at Fz. A separate electrode should be attached and connected to the ground. Commonly used ground electrode positions include the vertex (Cz), mastoid, earlobe (A1 or A2) or linked earlobes. See Odorn et al., ISCEV standard for clinical visual evoked potentials—(2016 update), found at VEP Standard 2016 draft 2016 Feb. 24 jv012.docx02-24 jv012.docx February 2016). The VEP subtracts the time locked data in response to the images presented which produces an EEG response. This signal, if averaged enough times will result in a signal that is produced by the image and not produced by random firing of the brain.

The apparatus will generally include an analog amplifier with filters. The amplifier preferably can produce a gain of 100 and an op amp set for a gain of 1.1. Which results in an overall gain of 1100 v/v and be capable of detecting signals of 2.7 mv. A suitable amplifier is available from Analogue Devices Inc. (Norwood, Mass. USA), Model AD 8232, that can provide this level of amplification.

The amplifier is connected to the programmable analogue/digital converter (A/D) device. A suitable A/D converter can be obtained from Measurement Computing Corporation, such as their Model 1608 FS, Signal averaging and analysis can be accomplished by commercially available software platforms such as DasyLab™ (Measurement Computing Corporation, Norton, Mass., USA) or MatLab™ (The Mathworks, Inc., Natick, Mass., USA)to perform standard VEP signal a calculations, signal averaging etc VEP data can also be generated for purposes of this invention using VEP apparatus from Diopsys Inc. (Pine Brook, N.J. USA), such as Diopsys' NOVA™ VEP testing system) or Konan Medical USA (Irvine, Calif. USA), such as Koran's EvokeDx™ VEP testing system. Equipment from other suppliers and manufacturers can also be used. The equipment should be modified to present both a known reference image and other images for which a determination of recognition is desired.

FIG. 1A is a flow diagram showing steps of the one aspect of the method in determining differences in latencies that occur between one particular face and several reference images to establish statistical reliability that the subject has previous knowledge of one or more particular faces, shown generally at 10. In the invention, a protocol for facial recognition involves the following steps: In Step #1 shown at 11, preparation of the subject's scalp and placement of electrodes is carried out, including measuring, reference, and ground electrodes, in the standard pattern placement. The measuring electrode is placed 2 cm above the inion, the bony bump at the back of the head. The reference electrode is 2 cm above the brow. The ground electrode is placed at the top of the head, halfway between the other 2 electrodes. In Step #2 shown at 15, the Ohm meter is used to check the impedance, resistance, of the electrodes. They must be less than 5K Ohms. At Step #3, shown at 20, a patch is placed over the left eye. Set up best spectacle correction for the subject in a trial frame in front of the right eye. Step #4, shown at 25, presents known pictures or known facial images (i.e. of a famous person, such as Bill Clinton; movie stars; famous individuals; family members of the subject; etc.), with the signal reversing every ¼ sec, for a total of 1.5 seconds, in the following manner, over the trial frame correction, if any: no prism; 2 prism diopters base up; 2 prism diopters base right; 2 prism diopters base down; and 2 prism diopters base left. In Step #5 shown at 30, random unknown photographs/unknown face images are presented, for 15 seconds each, in the same manner: no prism; 2 prism diopters base up; 2 prism diopters base right; 2 prism diopters base down; and 2 prism diopters base left. Step #6, a patch is placed over the right eye. Set up best spectacle correction for the subject in a trial frame in front of the right eye. Steps #4 and #5 are repeated in the same manner for the right eye as for the left.

Two (2) prism diopters produce an adequate delay to determine a recognized image from an unknown image, but not enough to determine if a subject has a personal knowledge of the image. People see images on television, movies, newspapers, magazine, on social media and computers all the time. Even though these images are recognizable to an individual, the or she may not actually know them. Personal contact with an individual makes memory stronger. Additional sensory input, such as smell, touch, and emotions, combine to strengthen the effects of memory, all of which result in shorter neurotransmission speeds.

The important point is that the images identified as known are truly known to the subject. In order to distinguish between an image previously seen and an image personally known, a greater separation in neurotransmission, i.e., the difference between the P-100 Latency of the unknown, the image previously seen, and the image personally known may be required. A change in the amount of prism diopters (one prism diopter is equal to one-centimeter deviation at one meter) bends the light. A prism of at least three (3) prism diopters, preferably four (4) diopters, is used to produce this increase and separation in neurotransmission. Higher prism diopter values can also be used up to any practical limits based on the size and thickness of the optic. For example, 5, 6, 8, 10, 12 or more diopter values may be used.

When 4 prism diopters were used in our research, the mean p-100 latency of a personally-known image was 96.45 millisecond (msec), with a standard deviation of 3.92 msec.

The mean p-100 latency of an unknown image was 108.59 msec, with a standard deviation of 5.61 msec. This difference in neurotransmission is so large that images can be sampled for shorter durations. Sampling speeds Data s presented at a rate of two (2) reversals per second. The more data points that are needed to produce measurable signals the longer it takes to collect it. If the signals are strong, less data points must be averaged to measure neurotransmission speed. The signals produced with a four-diopter prism were at least 10 microvolts from peak to trough. Measurable signals can be determined with less data points. When two prism diopters were used more data points had to be averaged. The averaging time was 15 seconds. With 4 prism diopters, averaging time of as little as 5 seconds produces a repeatable and measurable neurotransmission speed.

The subject protocol assumes that the best corrected visual acuity was between 20/20 and 20/60. The following are the prisms preferably used when visual acuity is worse than 20/60: 20/20 to 20/60, 4 Prism Diopters; 20/70 to 20/100, 6 Prism Diopters; 20/120 to 20/200, 8 Prism Diopters; More than 20/200, 10 Prism Diopters.

Figure 1B:
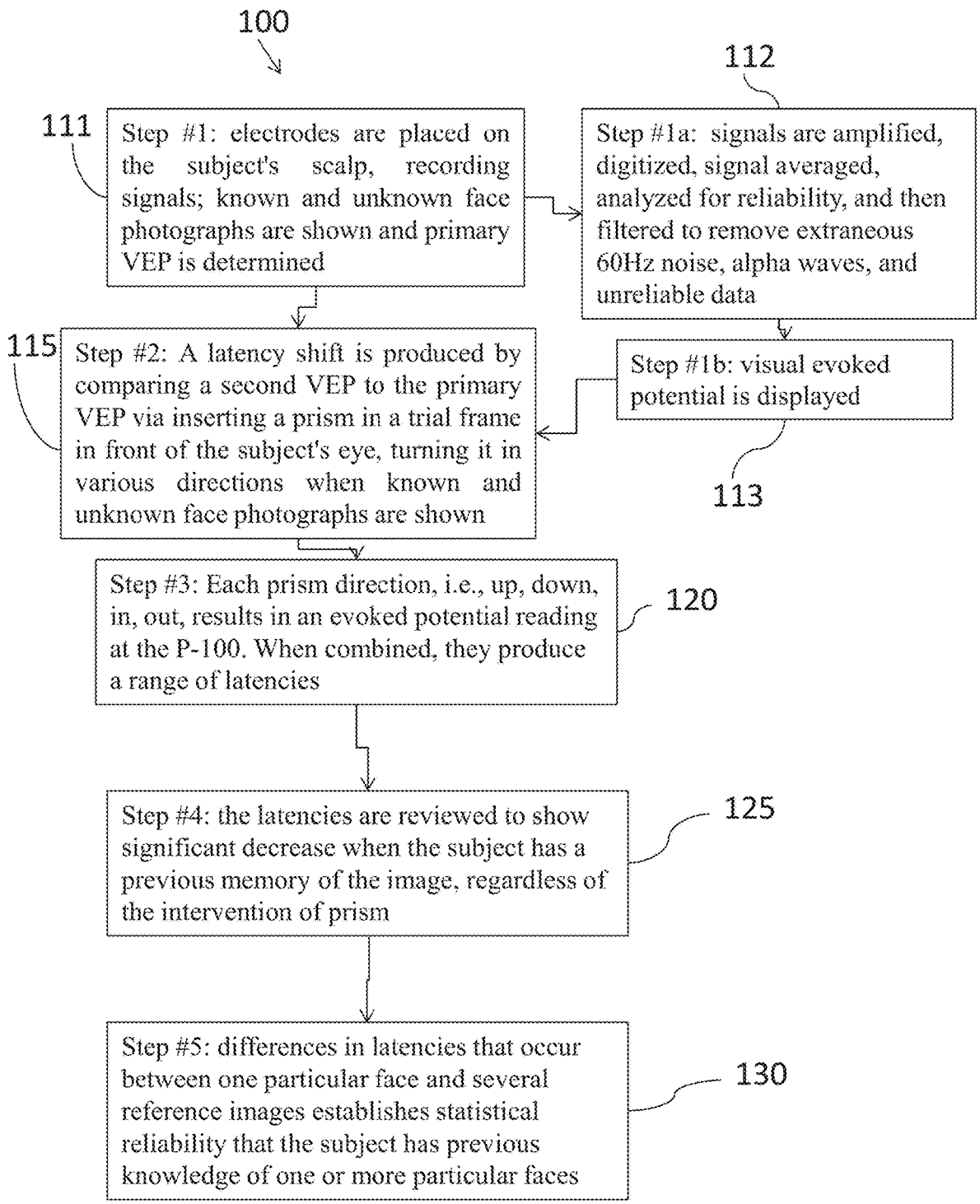
FIG. 1B is another flow diagram showing steps of a method for determining differences in latencies that occur between one particular face and several reference images to establish statistical reliability that the subject has previous knowledge of one or snore particular faces.

FIG. 1B is a flow diagram showing generally at 100 the steps of the method used to determine differences in latencies that occur between one particular face and several reference images to establish statistical reliability that the subject has previous knowledge of one or more particular faces. In Step #1, shown at 111 electrodes are placed on the subject's scalp for recording signals. In Step #1a, shown at 112 the signals are amplified, digitized, signal averaged, analyzed for reliability, and then filtered to remove extraneous 60 Hz noise, alpha waves, and unreliable data. The visual evoked potential is displayed at in Step #1b shown at 113. In Step #2 shown at 115 a latency shift is produced by inserting a prism in a trial frame in front of the subject's eye and turning it in various directions. At Step #3 shown at 120 each prism direction, i.e., up, down, left, right of the center of the retina, results in an evoked potential reading at the P-100 ERP. When combined, the ERP produce a range of latencies. In Step #4 shown at 125 the latencies are reviewed to determine a significant decrease when the subject has a previous memory of the image, regardless of the intervention of prism. At Step #5 shown at 130 the differences in latencies that occur between one particular face and several reference images establishes statistical reliability that the subject has previous knowledge of one or more particular faces.

FIG. 2 is a flow diagram showing generally at 200 the presentation of the image presentation and prism directions. Preferably the following presentation of the prism direction or image perception is shown to the patient: Up+Down 201 (reference image orientation and upside down; Rotated 202 (reference orientation and rotated); Inverted 203 (reference orientation and inverted); On+off 204 (reference orientation and off–no image); On Equi-luminant 205; and On +Grey 206 (reference orientation and solid gray image). Preferably, the ON and ALTERED visual images in the orientation sequence sire substantially equi-luminant, or of equal brightness, providing for minor changes in mean luminance during transition between images or image orientations in order to minimize or avoid any impact on VEP data. Any combination of the presentation of images 201-206 can be carried out or repeated as indicated at 207.

Figure 3A:
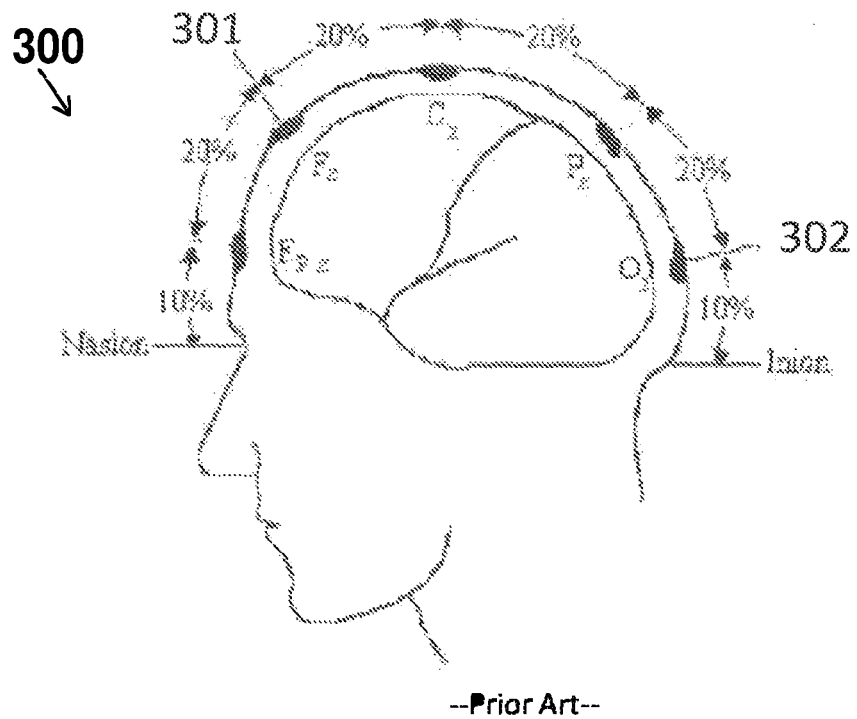
FIG. 3A is an illustration of a plan side view of a patient's head prepared for application of the method to determine objectively visual memory of faces, showing Step #1 of the method of FIG. 1B.
Figure 3B:
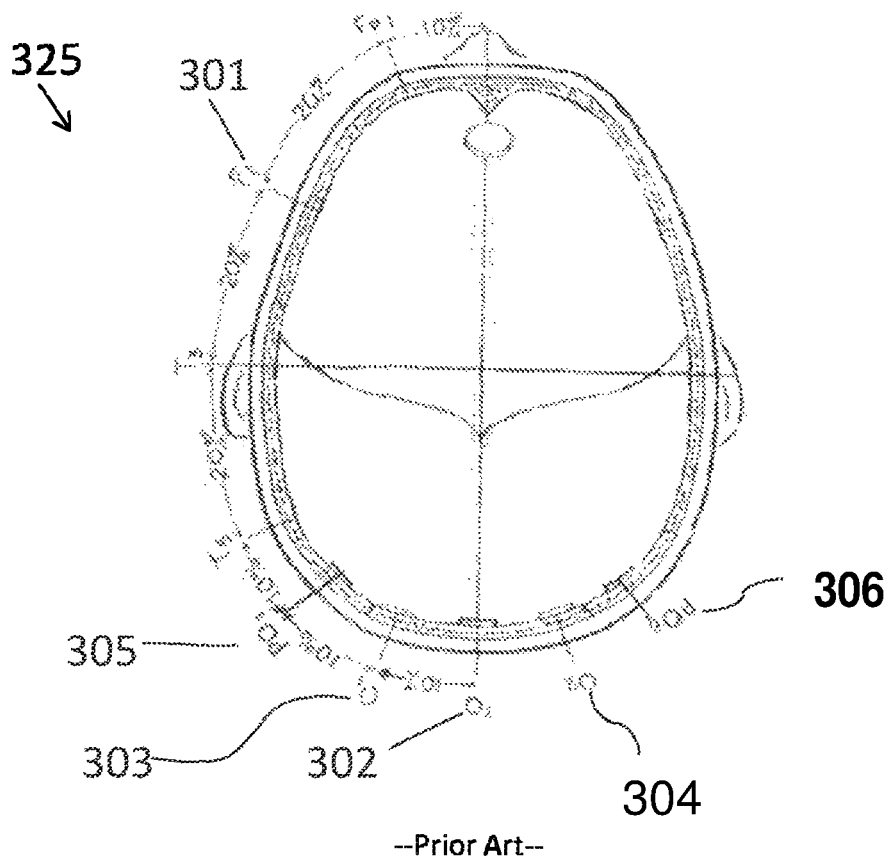
FIG. 3B shows a top cross-sectional view of the patient's head of FIG. 3A, shown at 325.

FIG. 3A shows generally at 300 an illustration of a plan side view of a patient's head prepared for application of the method to determine objectively visual memory of faces, showing Step #1 of the method of FIG. 1B. FIG. 3B shows a top cross-sectional view of the subject's head of FIG. 3A, shown at 325. Referring to FIGS. 3A and 3B, the location of active and reference Electrodes for Standard Responses are shown. A reference electrode 301 is placed at location Fz. An active electrode 302 is placed along the midline at Oz. Subscript z indicates a midline position. As illustrated in FIG. 3B, locations of lateral active electrodes are placed at O1 shown at 303, O2 shown at 304, PO7 shown at 305, and PO8 shown at 306 are indicated along with the midline active electrode 302 location, Oz.

Figure 3C:
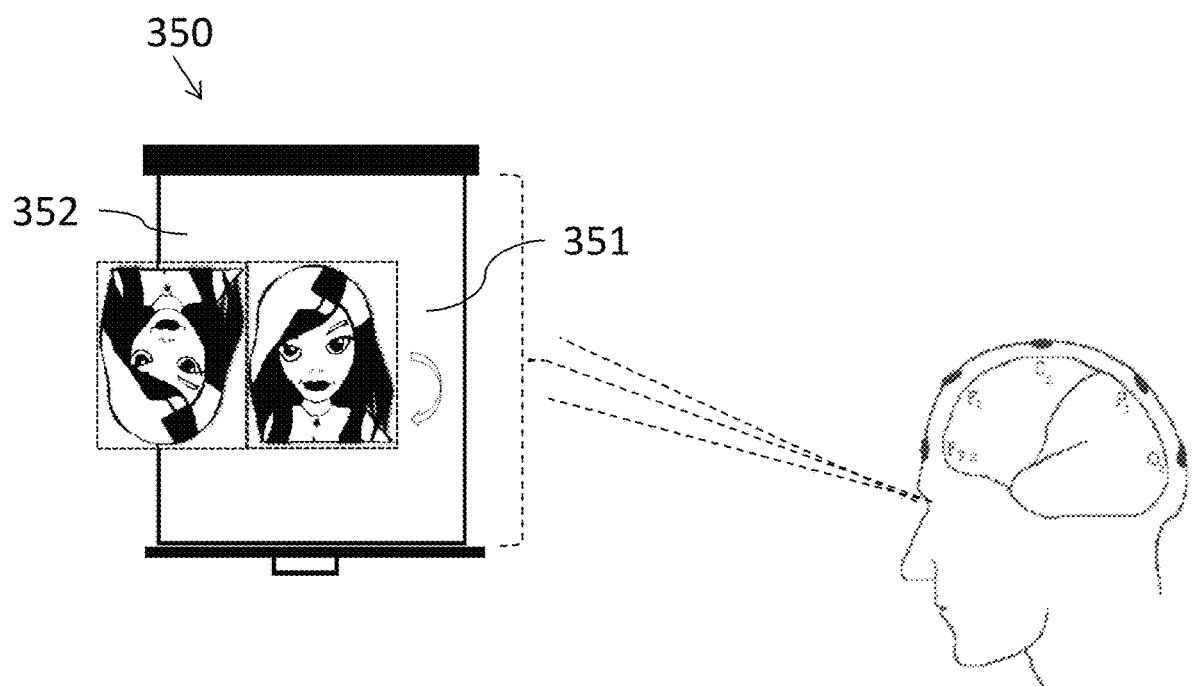
FIG. 3C is an illustration of Step #1*a* of the method of FIG. 1*b* and FIG. 2, wherein there is a presentation of images following signal amplification, digitizing, signal averaging, analyzing for reliability, and filtering to remove extraneous 60 Hz noise, alpha waves, and unreliable data.

FIG. 3C shows generally at 350 an illustration of Step #1a of the method of FIG. 1B and FIG. 2 wherein there is a presentation of images following signal amplification, digitizing, signal averaging, analyzing for reliability, and filtering to remove extraneous 60 Hz noise, alpha waves, and unreliable data. Facial images undergo image reversals and presentations shown generally at 351. The images are presented on a screen 352 in different orientations as set forth in FIG. 2. Timing of the stimuli, or image presentation orientations, preferably occur at 100 msec (measuring at P100). Preferably least two (2) reversals per second are used, more preferably between 2 and 10. The image should be alternated and not just presented as one steady image, or a measurable signal may not occur. International Standards typically suggest three (3) or four (4) image reversals per second. As the patient 352 views the flash images or image reversals 351 VEP is recorded and ERP measured. A visual evoked potential is displayed (for example, see FIGS. 4A-4C).

Figure 3D:
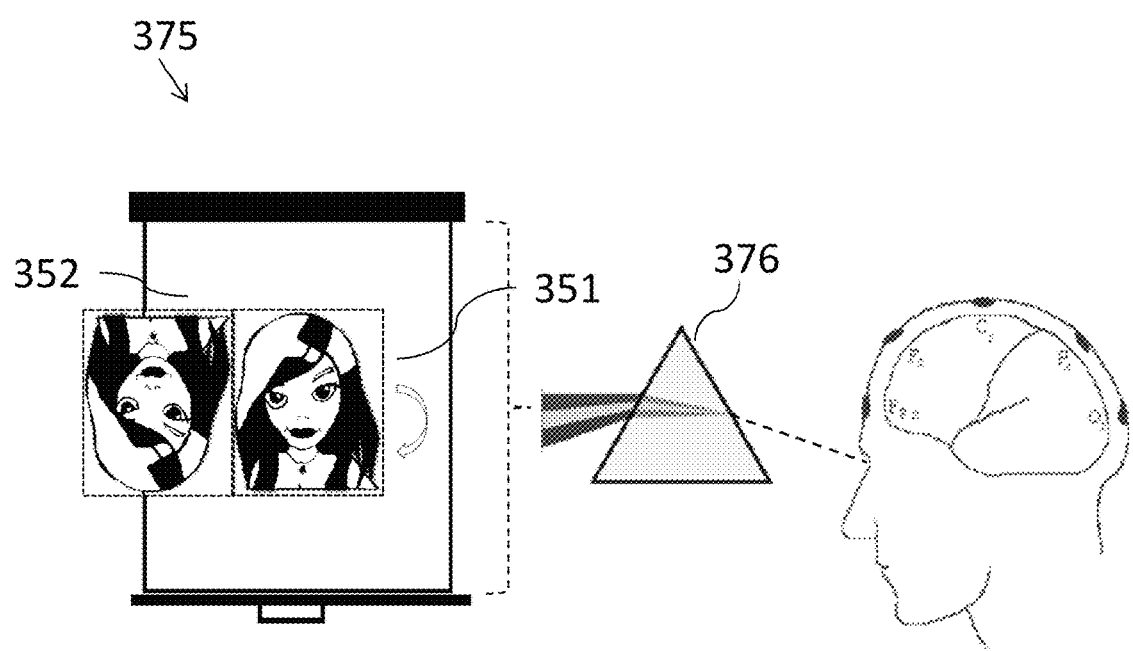
FIG. 3D is an illustration of Step #2 of the method of FIG. 1*b* and FIG. 2, wherein a latency shift is produced by inserting a prism in a trial frame in front of the subjects eye, turning it in various directions.

FIG. 3D shows generally at 375 an illustration of Step #2 of the method of FIG. 1B and FIG. 2, wherein a latency shift [i.e. primary VEP–secondary VEP] is produced by inserting a prism in a trial frame in front of the subject's eye, turning it in various directions. After displaying recorded visual evoked potentials in Step #1a and #1b, a prism 376 is presented in a trial frame in front of the subject/patient's eye. Each prism direction, i.e., up, down, left, right of the center of the retina [See FIG. 2] results in an evoked potential reading at the P-100. When combined, they produce a range of latencies. The latencies are reviewed to show significant decrease when the subject has a previous memory of the image, regardless of the intervention of prism (Step #4 in FIG. 1B). Differences in latencies that occur between one particular face and several reference images establishes statistical reliability that the subject has previous knowledge of one or lore particular faces (Step #5 in FIG. 1B).

Figure 4A:
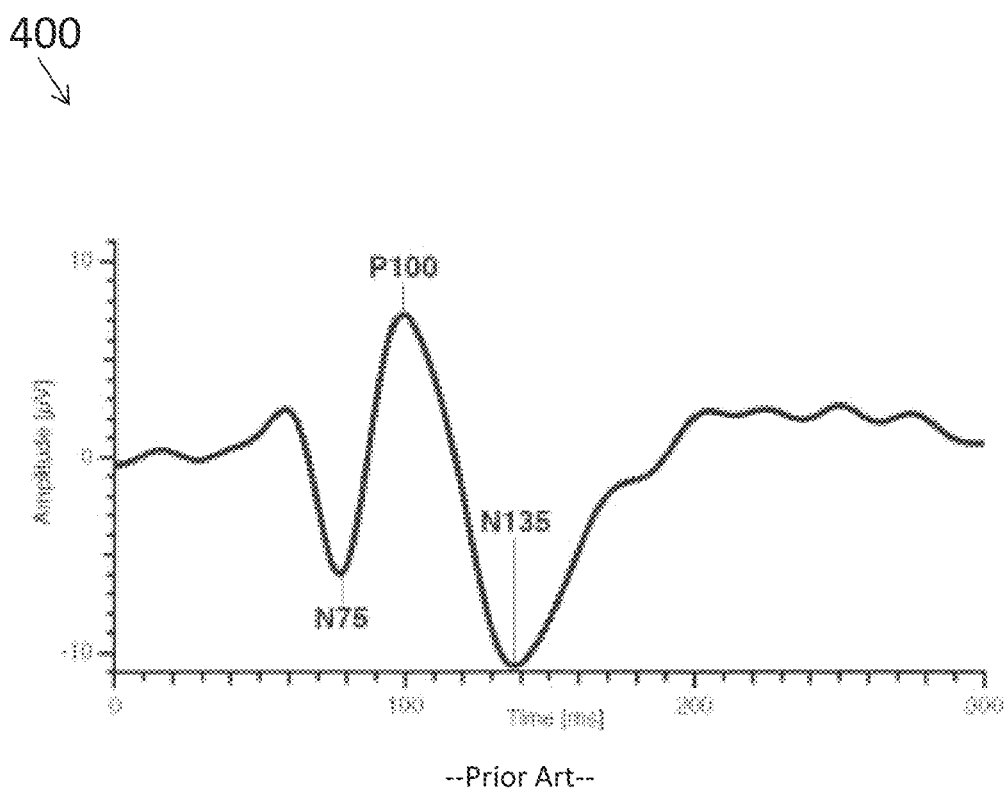
FIG. 4A illustrates a typical pattern reversal VEP.
Figure 4B:
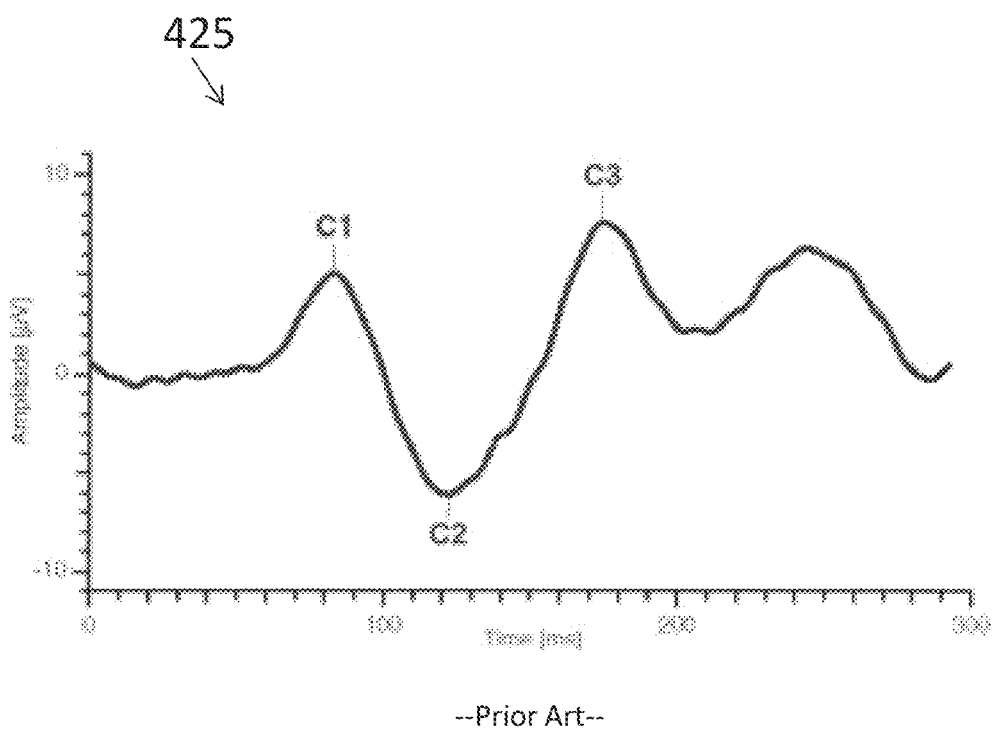
FIG. 4B illustrates a typical pattern onset/offset VEP.
Figure 4C:
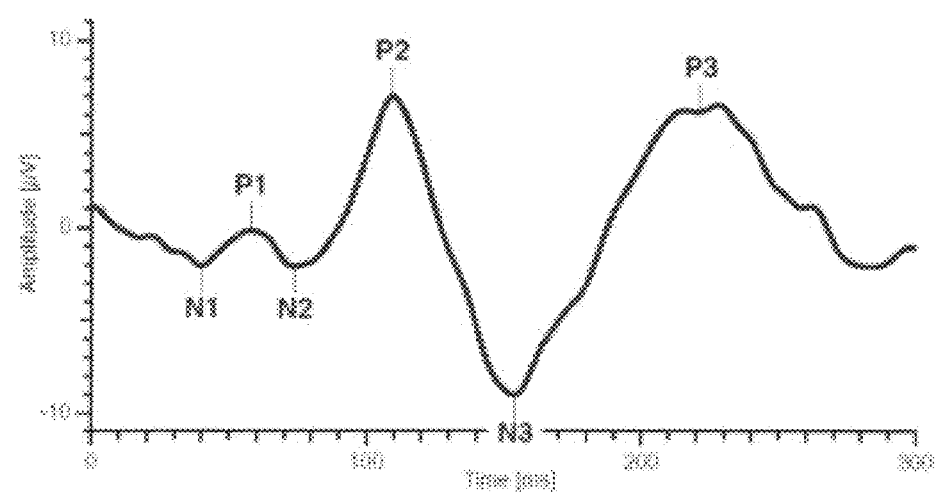
FIG. 4C illustrates a typical flash VEP.

FIGS. 4A-4C illustrate examples of event-related potentials (ERPs) or measured brain response that is the direct result of the specific sensory, cognitive, or motor event presented in the subject method. FIG. 4A illustrates a typical pattern reversal VEP shown at 400. FIG. 413 illustrates a typical pattern onsetloffset VEP shown at 425. Note that with a 300 ms sweep only the pattern onset response is recorded. FIG. 4C illustrates a typical flash VEP shown at 475.

FIGS. 5A-5B illustrate results of an example of a neurotransmission assessment, of a subject, subject P1, carried out by the method of FIG. 1A. FIG. 5A illustrates the method of FIG. 1A carried out on subject P1 showing computed results for the right eye; FIG. 5B illustrates the method of FIG. 1A carried out on subject Pi showing computed results for the left eye. The EEG signal for a specific image starting when it, is first flashed on FIG. 5A illustrates the method of FIG. 1A carried out on subject Pi showing computed results for the left and right eye wherein a known photograph face or image, Bill Clinton, was shown to the subject alternating in two orientations. P1 in this test was a 66-year-old male. The same method is used while viewing through a prism in different orientations. The same technique is used for an unknown image of a face. Known and unknown testing can be randomized. Testing is performed separately for right eye and left eye. Testing can be conducted using VEP apparatus from Diopsys Nova or Konan Medical suppliers. Other suppliers provide equipment that performs similar functions and can also be used. The research was performed using Diopsys Nova equipment, which was specially adapted to present faces of people that were known and unknown to the test subject. Each image was presented in a sequence of alternating image of the effect image and the inverted upside-down image.

FIGS. 6A-6B illustrate results of an example of a neurotransmission assessment of a subject, subject P2, carried out by the method of FIG. 1A. FIG. 6A illustrates results for the right eye; FIG. 6B illustrates results for the left eye, The EEG signal for a specific image starting when it is first flashed illustrates the method carried out on subject P2 showing computed results for the left and right eye wherein a known photograph face or image, Bill Clinton, was shown to the subject alternating in two orientations followed by random images. P2 in this test was a 25-year-old female. The same method is used while viewing through a prism in different orientations. The same technique is used for an unknown image of a face. Known and unknown testing can be randomized. Testing is performed separately for right eye and left eye. Testing can be conducted using VEP apparatus from Diopsys Inc. (Pine Brook, N.J. USA), such as Diopsys' NOVA™ VEP testing system) or Konan Medical USA (Irvine, Calif. USA), such as Konan's EvokeDx™ VEP testing system. Other suppliers provide equipment that performs similar functions and can also be used. The research was performed using Diopsys Nova equipment, which was specially adapted to present faces of people that were known and unknown to the test subject. Each image was presented in a sequence of alternating image of the effect image and the inverted upside-down.

FIGS. 7A-7B illustrate results of an example of a neurotransmission assessment of a subject, subject P3, carried out by the method of FIG. 1A. FIG. 7A illustrates results for the right eye; FIG. 7B illustrates results for the left eye, The EEG signal for a specific image starting when it is first flashed illustrates the method carried out on subject P3 showing computed results for the left and right eye wherein a known photograph face or image, Bill. Clinton was shown to the subject alternating in two orientations followed by random images. P3 in this test was a 25-year-old male. The same method is used while viewing through a prism in different orientations. The same technique is used for an unknown image of a face. Known and unknown testing can be randomized. Testing is performed separately for right eye and left eye. Testing can be conducted using VEP apparatus from Diopsys Nova or Konan Medical suppliers. Other suppliers provide equipment that performs similar functions and can also be used. The research was performed using Diopsys Nova equipment, which was specially adapted to present faces of people that were known and unknown to the test subject. Each image was presented in a sequence of alternating image of the effect image and the inverted upside-down image.

Figure 8A:
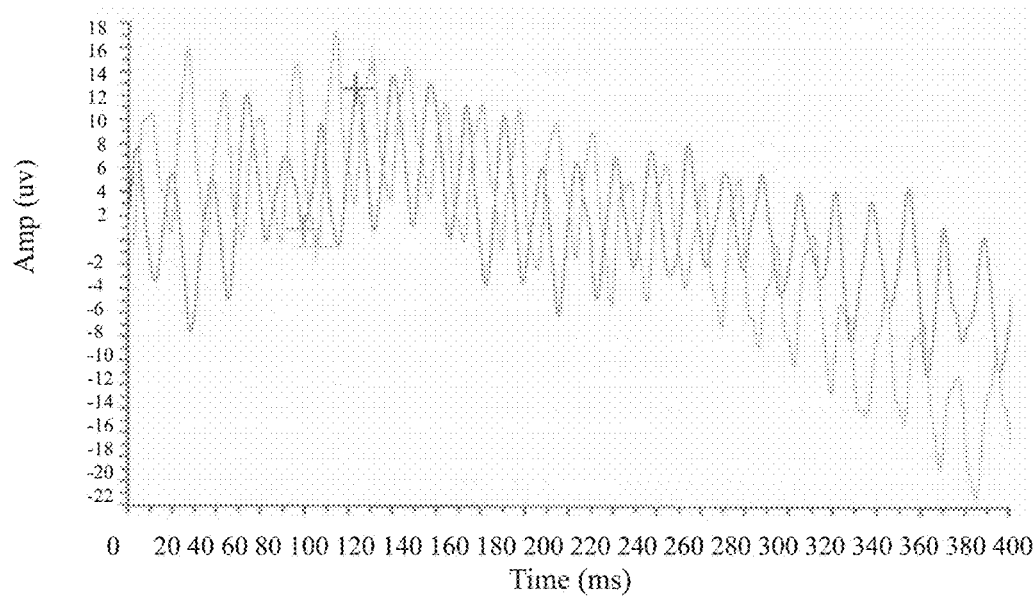
FIG. 8A shows the latency for a known image is less than an unknown image. The evoked potential for the right eye for subject P4 is presented. The left eye is patched and a prism is placed in front of the right eye. The prism is the same amount and direction for the known image (Bill Clinton) and the unknown image (Random). The Right Cursor Lat findings show that the latency for the known image is less than that for the unknown image.
Figure 8B:
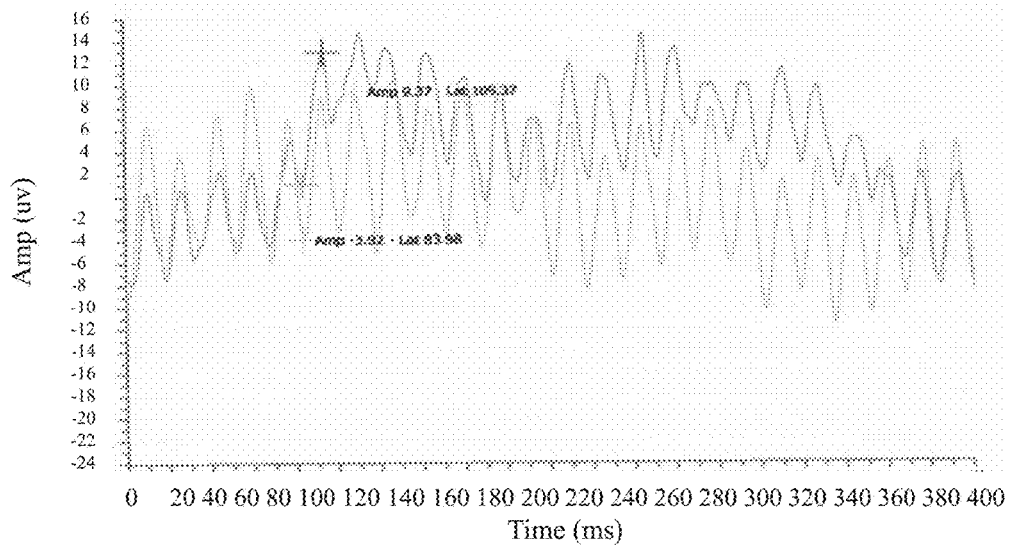
FIG. 8B shows the latency for a known image is less than unknown image. The evoked potential for the left eye for subject P4 is presented. The Right eye is patched and a prism is placed in front of the left eye. The prism is the sale amount and direction for the own it age (Bill Clinton) and the unknown image (Random). The Right Cursor Lat findings show that the latency for the known image is less than that for the unknown image.

FIGS. 8A-8B illustrate results of an example of a neurotransmission assessment of a subject, subject P4, carried out by the method of FIG. 1A. FIG. 8A illustrates results for the right eye; FIG. 8B illustrates results for the left eye. The EEG signal for a specific image starting when it is first flashed illustrates the method carried out on subject P4 showing computed results for the left and right eye wherein a known photograph face or image, Bill Clinton, was shown to the subject alternating in two orientations followed by random images. P4 in this test was a 73-year-old female. The same method is used while viewing through a prism in different orientations. The same technique is used for an unknown image of a face. Known and unknown testing can be randomized. Testing is performed separately for right eye and left eye. Other suppliers provide equipment that performs similar functions and can also be used. The research was performed using Diopsys Nova equipment, which was specially adapted to present faces of people that were known and unknown to the test subject. Each image was presented in a sequence of alternating image of the effect image and the inverted upside-down image.

FIGS. 9A-9B illustrate results of an example of a neurotransmission assessment of a subject, subject P5, carried out by the method of FIG. 1A. FIG. 9A illustrates results for the right eye; FIG. 9B illustrates results for the left eye, The EEG signal for a specific image starting when it is first flashed illustrates the method carried out on subject P5 showing computed5 results for the left and right eye wherein a known photograph face or image, Bill Clinton was shown to the subject alternating in two orientations followed by random images. P5 in this test was an 85-year-old male. The same method is used while viewing through a prism in different orientations, The same technique is used for an unknown image of a face. Known and unknown testing can be randomized. Testing is performed separately for right eye and left eye. The research was performed using Diopsys Nova equipment, which was specially adapted to present faces of people that were known and unknown to the test subject. Each image was presented in a sequence of alternating image of the effect image and the inverted upside-down image.

Those skilled in the art will appreciate that the invention improves upon methods and systems for initiating, measuring and performing VEP/VEP and EEG. The subject matter of this disclosure, and components thereof, can be realized by software instructions that upon execution cause one or more processing devices to carry out the processes and functions described above. Such instructions can, for example, comprise interpreted instructions, such as script instructions, e.g., JavaScript or ECMAScript instructions, executable code, or other instructions stored in a computer readable medium.

Implementations of the subject matter and the functional operations described in this specification can be provided in digital electronic circuitry, or in computer software, firmware, or hardware, including the structures disclosed in this specification and their structural equivalents, or in combinations of one or more of them. Embodiments of the subject matter described in this specification can be implemented as one or more computer program products, i.e., one or more modules of computer program instructions encoded on a tangible program carrier for execution by, or to control the operation of, data processing apparatus.

In the preferred method, a first image shown to the subject is a reference image that the subject knows, such as an image of the subject himself/herself. After the subject views the image using two or more prism orientation directions, the VEP corresponding to the prism orientation direction with the shortest latency is selected and used for viewing all other, or target, images. The latency for the target image is compared to the latency for the reference image to determine whether the subject knows or has personal knowledge of the target image.

As previously discussed, the latency preferably utilized from the VEP data is the P-100 Latency. As will be well understood by those skilled in the art, the P-100 latency refers to the peak in the VEP data that typically occurs at about 100 milli-seconds after exposure to a visual stimulus. For any individual or exposure to a visual stimulus, the actual peak reflected in the data can vary above or below 100-milli-seconds, depending on the physiology of the subject, the image that is shown, and the image presentation variables including those discussed herein. When the latency of the target image is longer than the latency of the target image to a statistically significant amount, I have found according to this invention that such slower transmission speed correlates to the subject not having personal knowledge of the image. Conversely, when the latency for the target image is the same as the reference image, or is not statistically significantly different, that correlates with the subject having personal knowledge of the subject matter depicted in the target image.

A computer program (also known as a program, software, software application, script, or code) can be written in any form of programming language, including compiled or interpreted languages, or declarative or procedural languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program) in question, or in multiple coordinated files (e.g., files that store one or more modules, sub programs, or portions of code). The processes and logic flows described in this specification are performed by one or more programmable processors executing one or more computer programs to perform functions by operating on input data and generating output, thereby tying the process to a particular machine (e.g., a machine programmed to perform the processes described herein).

Computer readable media suitable for storing computer program instructions and data include all forms of nonvolatile memory, media and memory devices, including by way of example semiconductor memory devices (e.g., EPROM, EEPROM, and flash memory devices); magnetic disks (e.g., internal hard disks or removable disks); magneto optical disks; and CD ROM and. DVD ROM disks. The processor and the memory can be supplemented by, or incorporated in, special purpose logic circuitry.

Thus, the invention also provides a non-transitory computer storage readable medium for determining latency shift in Visual Evoked Potential (VEP) between two or more images , comprising computer-useable instructions that, when used by one or more computing devices, cause the one car more computing devices to: receive information from electrodes on a subject's scalp generating and recording EEG signals corresponding to synaptic transmission/neurotransmission speed when a subject is presented with a series of visual stimuli corresponding to said image presented in an orientation sequence based on a timing cycle; receive info nation from electrodes on a subject's scalp generating acid recording EEG signals corresponding to synaptic transmission/neurotransmission speed when a subject is presented with at least one prism placed in front of said series of visual stimuli corresponding to said image; wherein EEG signals evoked in response to said visual stimuli and said prism placed in front of said visual stimuli are evoked and processed by a processor to provide a the VEP, and. wherein said medium further includes instructions for determining VEP for two or more images and for determining the presence of a latency shift between said two or more images, especially the P-100 Latency.

Having thus described the invention in rather full detail, it will be understood that, such detail need not be strictly adhered to, but that additional changes and modifications may suggest themselves to one skilled in the art, all falling within the scope of the invention as defined by the subjoined claims.

The invention claimed is:

1. A method for determining latency shift in Visual Evoked Potential (VEP) between at least two or more images including a target image that is useful for determining visual recognition of the target image, comprising the steps of:
   a. presenting a series of visual stimuli corresponding to said target image to a subject to evoke a first VEP wherein a prism having a specific prism direction relative to a retina and a diopter value of two or more is provided between said target image and said subject, said visual stimuli of said target image being presented in an orientation sequence based on a timing cycle, said timing cycle having ON and ALTERED phases that are substantially equi-luminant, said target image comprising a person, a place, or an object;
   b. presenting a second series of visual stimuli corresponding to a second image to said subject to evoke a second VEP wherein the prism having the specific prism direction is provided between said second image and said subject, said visual stimuli of said second image being presented in an orientation sequence based on a timing cycle, said timing cycle having ON and ALTERED phases that are substantially equi-luminant, said second image comprising a person, a place, or an object;
   c. recording the first VEP and the second VEP and determining whether there is a latency shift between the first VEP and the second VEP based on P-100 latency times.

2. The method of claim 1, wherein said two images comprise at least one reference image that the subject knows and said target image.

3. The method of claim 2, wherein said method is used for determining visual recognition of an image by the subject by comparing latency shift of the reference image to the target image.

4. The method of claim 2, wherein the target image is an image of an object or person with which a person administering the method believes the subject has seen but does not have a personal relationship.

5. The method of claim 1, wherein at least one image presented to the subject is obtained from an internet-based social media platform.

6. The method of claim 1, wherein said first and second VEPs are determined based on signal averaging of the series of visual stimuli corresponding to the respective first and second VEPs.

7. The method of claim 1, wherein the diopter value is 4 or more diopters.

8. The method of claim 1, wherein the prism can be adjusted to direct the image to at least 4 different directions relative to the retina of the subject.

9. The method of claim 1, wherein said prism can be adjusted in directions comprising up, down, left, and right relative to a center of the retina of the subject.

10. The method of claim 1, wherein said orientation sequences comprise an ON phase for a particular image and an ALTERED phase for the image that is different from the particular image.

11. The method of claim 10, wherein the ALTERED phase comprises an altered image of the particular image, a blank image, a pattern, or an abstract design.

12. The method of claim 10, wherein the particular image in the ALTERED phase is the particular image in a different orientation, the orientation being selected from the group consisting of upside down, inside out, inverted, rotated, and combinations thereof.

13. The method of claim 1, wherein there are between 2 and 10 reversals per second in the orientation sequence.

14. A non-transitory computer readable storage medium for determining latency shift in Visual Evoked Potential (VEP) between two or more images including a target image that is useful for determining visual recognition of the target image, comprising computer executable instructions that, when executed by one or more computing devices, cause the one or more computing devices to:

determine a specific prism direction relative to a retina of a prism having a diopter value of two or more;

receive information from electrodes on a subjects scalp generating and recording EEG signals corresponding to synaptic transmission speed when the subject is presented with a series of visual stimuli corresponding to said target image presented in an orientation sequence based on a timing cycle, said timing cycle having ON and ALTERED phases that are substantially equi-luminant, wherein said target image comprises a person, place, or object, wherein the information is associated with the specific prism direction; and receive information from the electrodes on the subject's scalp generating and recording EEG signals corresponding to synaptic transmission speed when the subject is presented with a second series of visual stimuli corresponding to a second image presented in an orientation sequence based on a timing cycle, said timing cycle having ON and ALTERED phases that are substantially equi-luminant, said second image comprising a person, a place, or an object, wherein the information is associated with the specific prism direction;

wherein the EEG signals evoked are recorded and processed by the computing device to provide VEPs corresponding respectively to the target image and the second image, and wherein said medium further includes instructions for determining whether there is a latency shift between the respective VEPs based on P-100 latency times.

15. The non-transitory computer readable storage medium as in claim 14, wherein said target image and said second image comprise a person or place.

* * * * *